US010525147B2

(12) United States Patent
Bozkurt et al.

(10) Patent No.: US 10,525,147 B2
(45) Date of Patent: Jan. 7, 2020

(54) BIONANOCOMPOSITE SYNTHESIS FOR WOULD HEALING

(71) Applicant: Imam Abdulrahman Bin Faisal University, Dammam (SA)

(72) Inventors: Ayhan Bozkurt, Dammam (SA); Abdulhadi Baykal, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/895,600

(22) Filed: Feb. 13, 2018

(65) Prior Publication Data

US 2019/0247514 A1    Aug. 15, 2019

(51) Int. Cl.
| | | |
|---|---|---|
| *A61K 47/36* | (2006.01) | |
| *A61K 47/69* | (2017.01) | |
| *A61K 9/00* | (2006.01) | |
| *A61K 9/51* | (2006.01) | |
| *A61P 17/02* | (2006.01) | |

(52) U.S. Cl.
CPC ........ *A61K 47/6923* (2017.08); *A61K 9/0014* (2013.01); *A61K 9/5115* (2013.01); *A61K 9/5192* (2013.01); *A61K 47/36* (2013.01); *A61P 17/02* (2018.01)

(58) Field of Classification Search
CPC .......... A61K 47/36; A61K 47/69; A61K 9/00; A61K 9/51; A61P 17/02
See application file for complete search history.

(56) References Cited

U.S. PATENT DOCUMENTS 10,183,093 B2 *  1/2019  McInnes ............... A61K 35/15

FOREIGN PATENT DOCUMENTS

| CN | 102108172 A | 6/2011 |
|---|---|---|
| CN | 104721875 A | 6/2015 |
| CN | 105169460 A | 12/2015 |

OTHER PUBLICATIONS

Ana M. Diez-Pascual, et al., "Wound Healing Bionanocomposites Based on Castor Oil Polymeric Films Reinforced with Chitosan-Modified ZnO Nanoparticles", BioMACROMOLECULES, vol. 16, No. 9, 2015, pp. 2631-2644.
Xiaodong She, et al.. "Functionalization of Hollow Mesoporous Silica Nanoparticles for Improved 5-FU Loading", Journal of Nanomaterials, vol. 2015, pp. 1-10.
Lizhang Sun, et al., "Novel Chitosan-Functionalized Spherical Nanosilica Matrx As an Oral Sustained Drug Delivery System for Poorly Water-Soluble Drug Carvedilol", ACS Applied Materials & Interfaces, vol. 5, No. 1, 2013, pp. 103-113.
Ziwei Deng, et al., "Hollow chitosan-silica nanospheres as pH-sensitive targeted delivery carriers in breast cancer therapy", Biomaterials, vol. 32, Issue 21, Jul. 2011, pp. 4976-4986.
Ayse Aslan, et al., "Synthesis and characterization of novel multifunctional polymer grafted hollow silica spheres", Journal of Materials Research, vol. 30, Issue 16, Aug. 28, 2015, pp. 2408-2416.
Qiong Jiang, et al., "Hypromellose succinate-crosslinked chitosan hydrogel films for potential wound dressing", International Journal of Biological Macromolecules, vol. 91, Oct. 2016, pp. 85-91.
Shahrzad Sirak Hassan Kiadeh, et al., "Preparation of chitosan-silica/PCL composite membrane as wound dressing with enhanced cell attachment", Polymers for Advanced Technologies, vol. 28, Issue 11, Nov. 2017, pp. 1396-1408.

* cited by examiner

*Primary Examiner* — Zohreh A Fay
(74) *Attorney, Agent, or Firm* — Oblon, McCelland, Maier & Neustadt, L.L.P.

(57) ABSTRACT

A method for treating a burn, lesion, lacuna, or wound comprising contacting the burn, lesion, or wound with a chitosan-functionalized silica sphere ("CHI-HSS"). Chitosan-functionalized silica spheres and pharmaceutical compositions containing them.

19 Claims, 15 Drawing Sheets

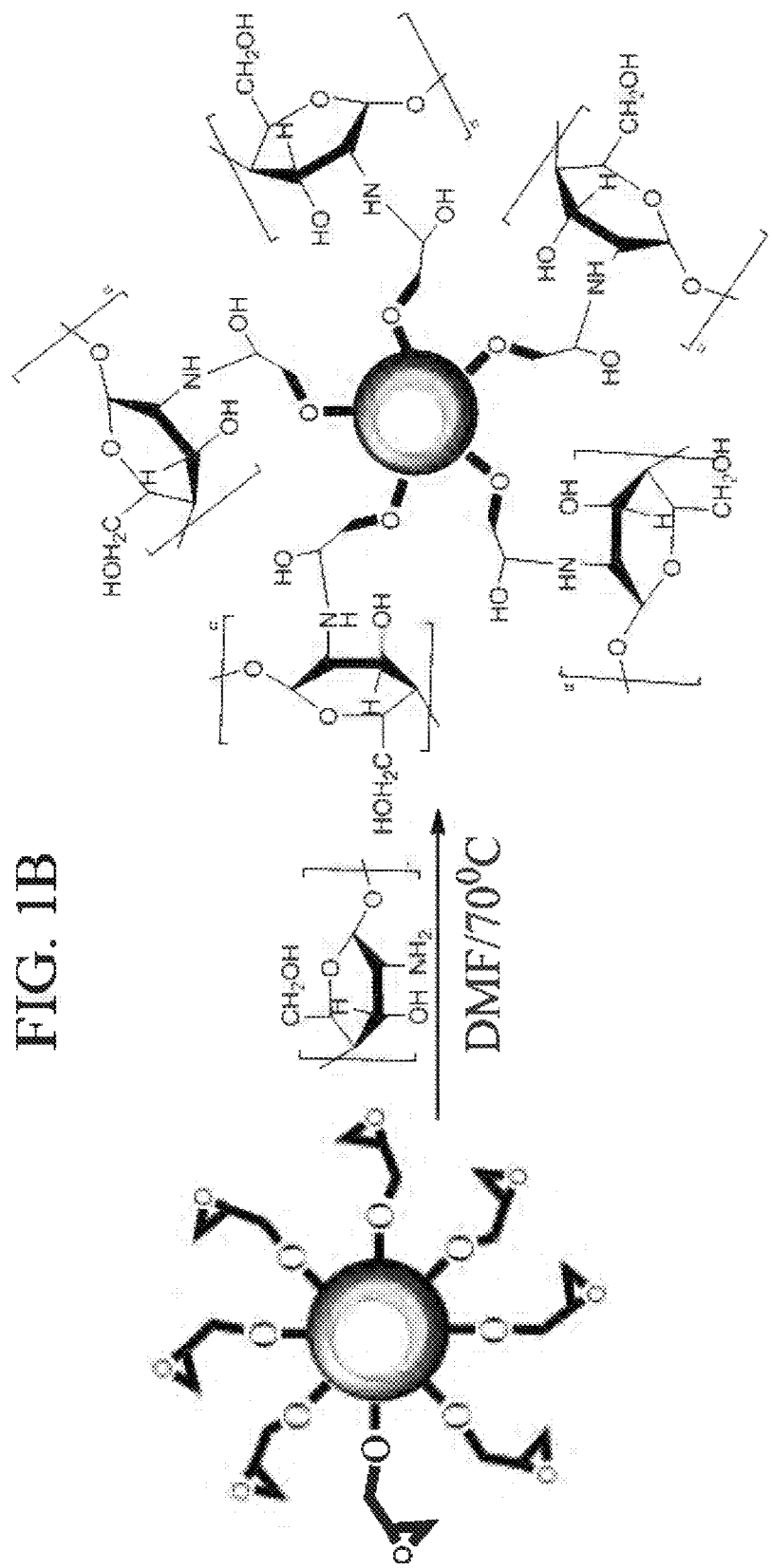

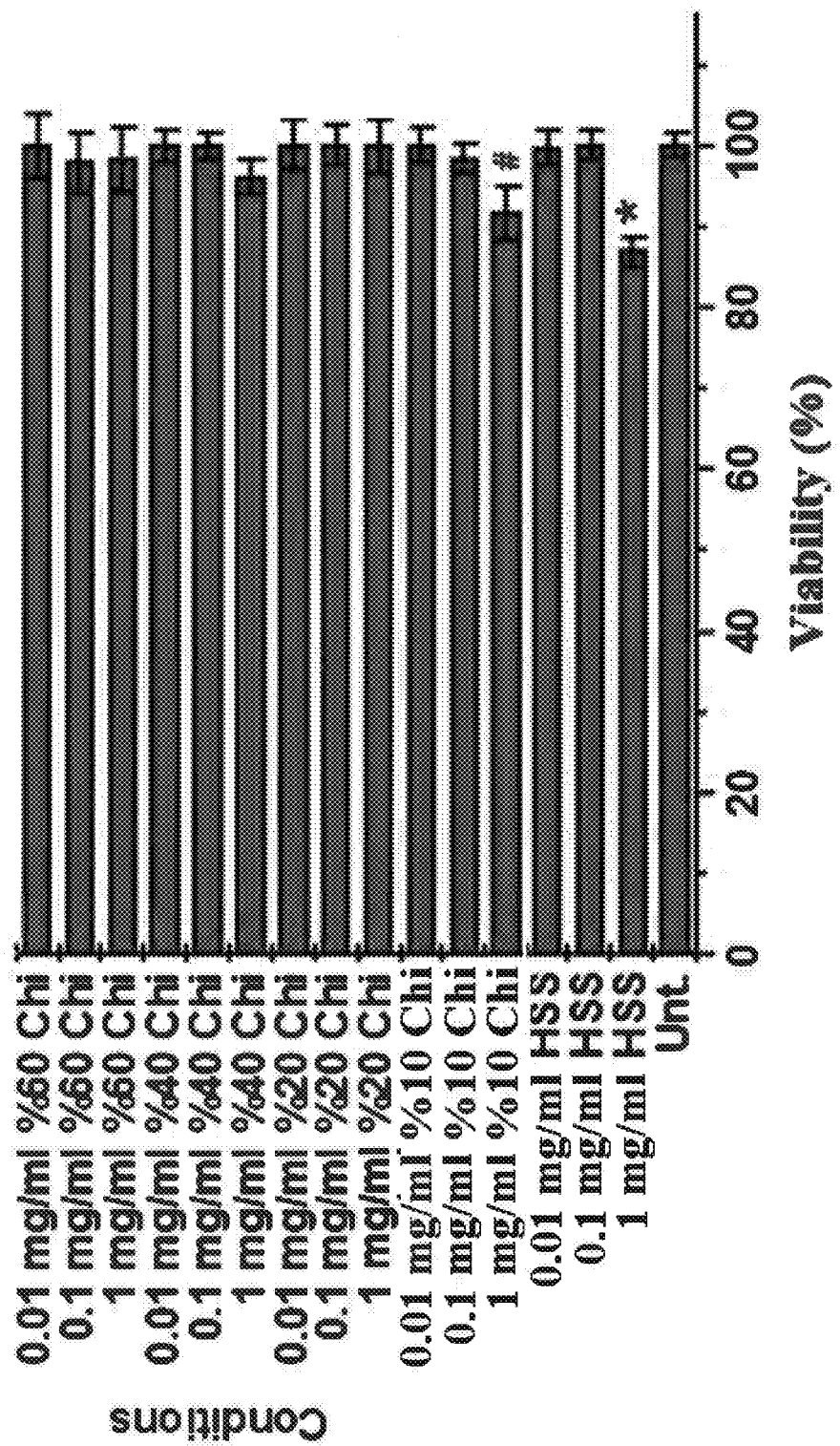

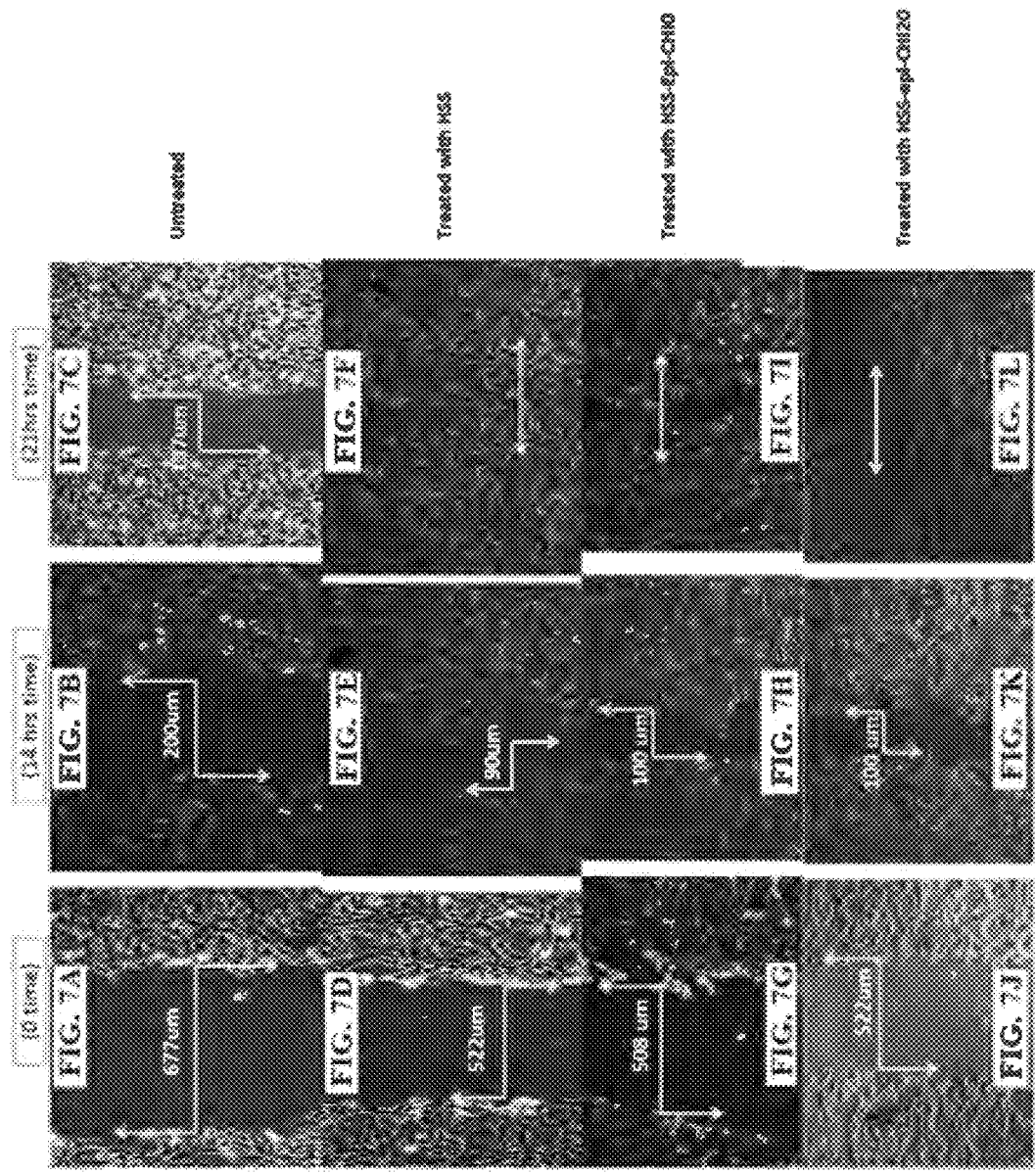

Figure 1A:
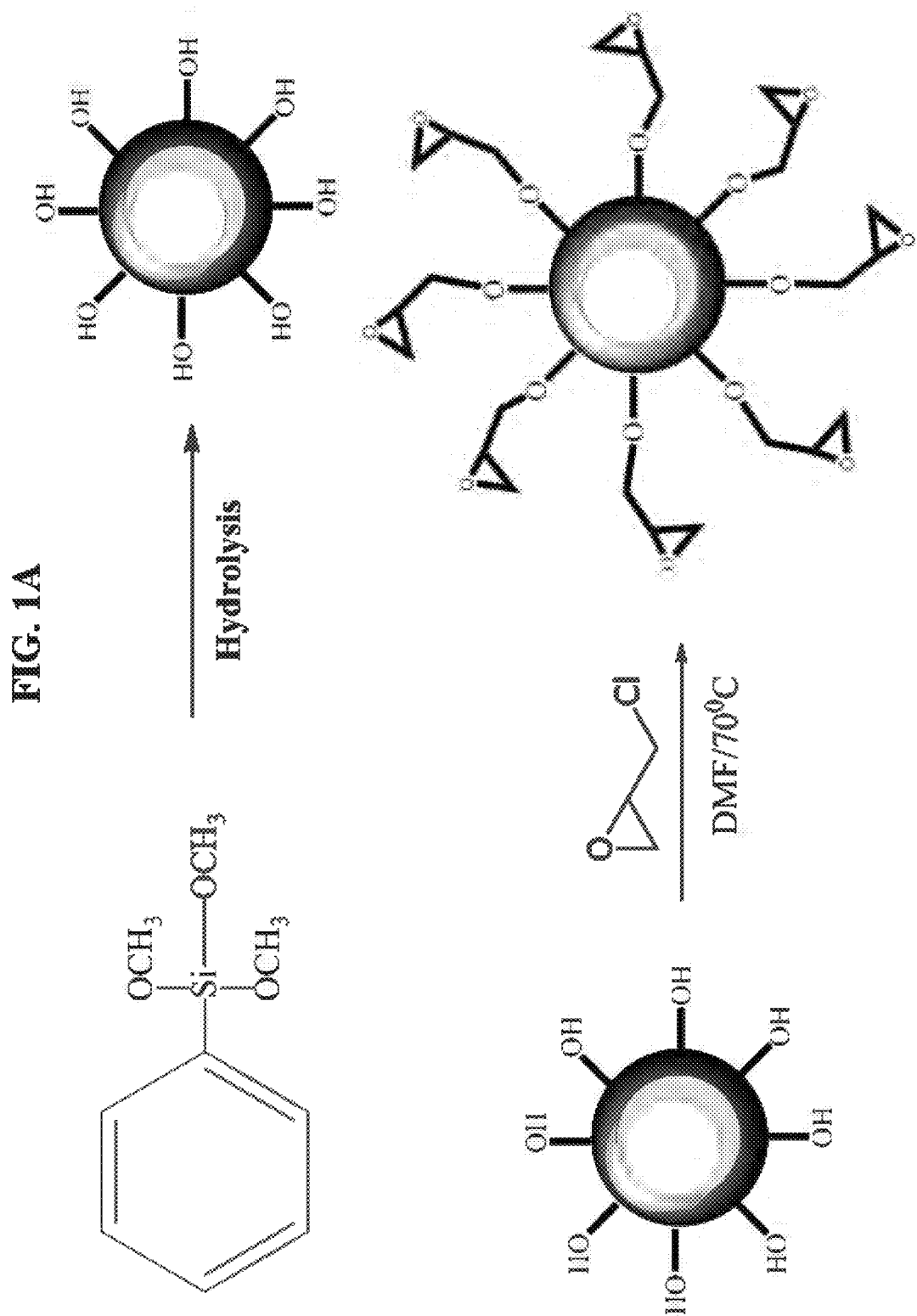

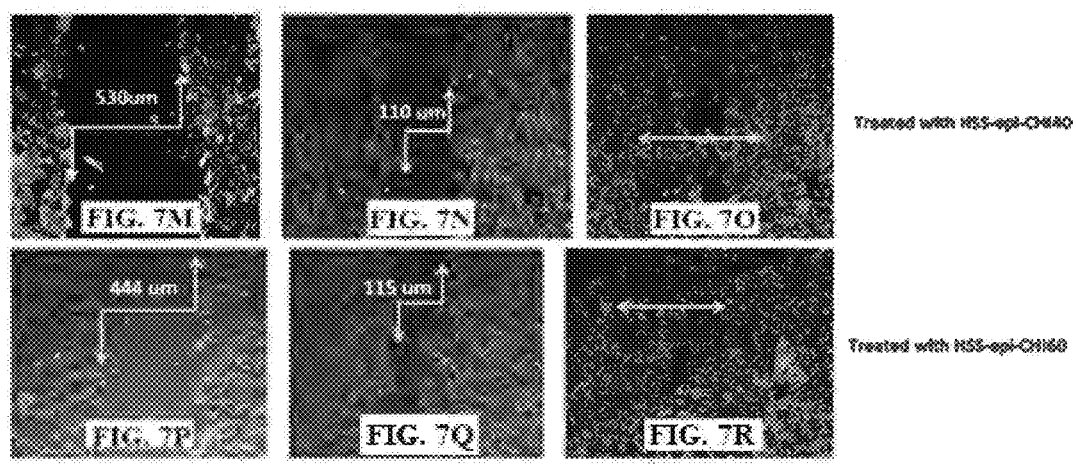
FIG. 8
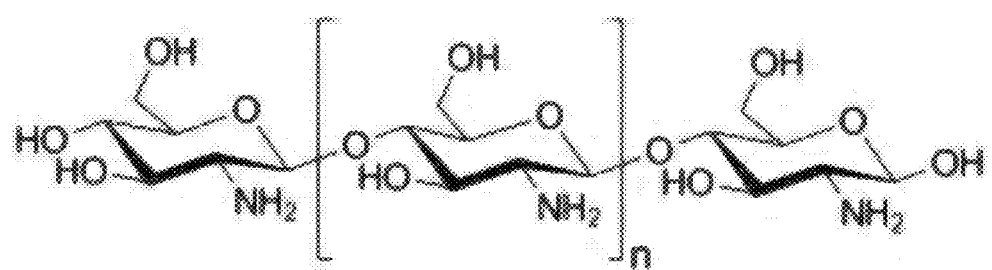

BIONANOCOMPOSITE SYNTHESIS FOR WOULD HEALING

BACKGROUND OF THE INVENTION

Field of the Invention

A method for wound healing by contacting a wound with a bionanocomposite comprising hollow silica spheres functionalized with the biopolymer chitosan.

Description of Related Art

Chitosan is a copolymer which consists of β-(1β4)-linked 2-acetamido-2-deoxy-D-glucopyranose and 2-amino-2-deoxy-D-glucopyranose units. Compared to other biopolymers like cellulose or starch, the processing of chitosan is simple because it is soluble in acidic aqueous solutions which facilitate the development of chitosan based materials. This solubility depends in part on the distribution of amino and N-acetyl groups in chitosan. Chitosan is readily available and inexpensive because it can be produced by deacetylation of chitin a biopolymer abundant in the exoskeletons of shrimp, crabs and other crustaceans.

Chitosan is a biopolymer having several advantageous biological properties including non-toxicity, biocompatibility, biodegradability, antimicrobial properties, and anti-inflammatory and wound-healing properties. Chitosan has been incorporated into various products including mouth washes and ingestible weight loss products. It biodegradable and can be metabolized by human enzymes such as lysozyme can metabolize chitosan.

Extensive studies are going on the development of chitosan based biomaterials for various biomedical applications such as wound healing, wound dressing, tissue engineering and drug delivery. Chitosan is effective in wound healing as it stimulates hemostasis and accelerates tissue regeneration. In wound healing, the biochemical functions of chitin and chitosan are fibroblast activation, cytokine production, giant cell migration and simulation of type IV collagen synthesis; see Muzzarelli, R. A. A. (2009). Chitins and chitosans for the repair of wounded skin, nerve, cartilage and bone. *Carbohydrate Polymers*, 76(2), 167-182.). Another feature of chitosan is its biodegradability; certain human enzymes like lysozyme can metabolize chitosan. N-acetyl glucosamine, the monomeric unit of chitosan, is very essential in wound repair. Anti-microbial activity of chitosan has been evaluated against various micro-organisms such as fungi, bacteria, and yeast; see Ahmad, M., Jayachandran, M., Qureshi, M. A & Ikram, S. (2015). *Chitosan based dressings for wound care. Immunochemistry & Immunopathology. Open Access* 1:106. doi: 10.4172/2469-9756.1000106. Antimicrobial property of chitosan arises from its cationic nature. Chitosan interacts with endotoxins of gram negative bacteria and decreases its acute toxicity. Antimicrobial activity of chitosan can be utilized in wound care as it can reduce the chances of infection by inhibiting the bacterial growth. The presence of bacteria delays the wound healing by contaminating wound surfaces and accessing the underlying tissues. Chitosan also possesses anti-inflammatory properties. When chitosan based material is applied as topical medicine on open wounds or cuts, it provides pain relief, cooling and soothing effect; see Ahmed, S., & Ikram, S. (2016). *Chitosan based scaffolds and their applications in wound healing. Achievements in the Life Sciences*, 10(1), 27-37. http://_doi.org/10.1016/j.als.2016.04.001.

Chitosan based materials can be easily processed in the form of gels, membranes, sponges, fibrils, beads, scaffolds, nanoparticles etc. Zhou et al. (2008) prepared a wound dressing material based on polyvinyl alcohol and carboxyethyl chitosan nanofibers via electro-spinning and studied the L 929 cell attachment and proliferation on the fibrous mats; see Zhou, Y., Yang, D., Chen, X., Xu, Q., Lu, F., & Nie, J. (2008). *Electrospun water-soluble carboxyethyl chitosan/poly(vinyl alcohol) nanofibrous membrane as potential wound dressing for skin regeneration. Biomacromolecules*, 9, 349-354. In another study, polyvinyl alcohol, carboxyethyl chitosan and silk fibroin nanoparticles having good biocompatibility and skin regeneration capacity were developed; see Zhou, Y., Yang, H., Liu, X., Mao, J., Gu, S., & Xu, W. (2013). Electrospinning of carboxyethyl chitosan/poly(vinyl alcohol)/silk fibroin nanoparticles for wound dressings. *International Journal of Biological Macromolecules*, 53, 88-92. http://_doi.org/10.1016/j.ijbiomac.2012.11.013. Van, Van and Ming-Fa (2013) developed curcumin/chitosan/gelatin composite sponge having improved water uptake ability, wound closure and antibacterial activity; see Van, C. N., Van, B. N., &. Ming-Fa, H. (2013). *Curcumin-loaded chitosan/gelatin composite sponge for wound healing application. International Journal of Polymer Science*, 2013, 106570. http://_dx.doi.org/10.1155/2013/106570. In another work, chitosan hydrogel was prepared for wound dressing and cell viability tests were conducted using fibroblast cells isolated from rat skin (Ribeiro, M. P., Espiga, A., Silva, D., Baptista, P., Henriques, J., Ferreira, C., Silva, J. C., Borges, J. P., Pires, E., Chaves, P., & Correia, I. J. (2009). *Development of a new chitosan hydrogel for wound dressing. Wound Repair and Regeneration*, 17(6), 817-824. https://_doi.org/10.1111/j.1524-475X.2009.00538.x). The authors reported that chitosan hydrogel promoted cell adhesion and proliferation and chitosan and its degradation by products were non cytotoxic. Another group developed chitosan/polyethylene glycol diacrylate blend films for wound dressing applications and evaluated the in vitro cytotoxicity of the films using L929 mouse fibroblasts. The materials showed good biocompatibility and noncytotoxicity; see Zhang, Z., Yang, D., & Nie, J. (2008). *Chitosan/polyethylene glycol diacrylate films as potential wound dressing material. International Journal of Biological Macromolecules*, 43, 456-462.

The advancement of nanotechnology has resulted in the development of nanoparticle based systems for applying in tissue engineering and skin repairing. Because of the large surface area to volume ratio of nanoparticles, they exhibit better activity. For decades, organic and/or inorganic nanomaterials such as polymers, dendrimers, liposomes, micelles, carbon, iron oxide, silicon, silver or gold based materials with different morphologies like nanotubes, nanowires, nanocapsules, nanofilms, nano gels have been fabricated and explored as new platforms for diagnostic and therapeutic purposes; see Deng, Z., Zhen, Z., Hu, X., Wu, S., Xu, Z., & Chu, P. K. (2011); *Hollow chitosan-silica nanospheres as pH-sensitive targeted delivery carriers in breast cancer therapy. Biomaterials*, 32(21), 4976-4986; https://_doi.org/10.1016/j.biomaterials.2011.03.050.

Among the various inorganic nanoparticles, silica particles have attracted much interest because of their excellent chemical stability, inert nature, thermal stability, low density, low toxicity and biocompatibility. Silica nanoparticles possess good compatibilities with other materials and can also functionalized easily for chemically binding to other active materials.

Over the past decades research has been conducted on mesoporous silica nanoparticles and hollow silica sphere ("HSS") nanoparticles. Because of large surface area, stability and biocompatibility, these silica nanoparticles have been used in various biomedical, pharmaceutics and biochemistry applications; see Liberman, A., Mendez, N., Trogler, W. C., &. Kummel, A. C. (2014). *Synthesis and surface functionalization of silica nanoparticles for nanomedicine. Surface Science Reports,* 69(2-3), 132-158; https://_doi.org/10.1016/j.surfrep.2014.07.001; Gui, R., Wang, Y., & Sun, J. (2014). *Embedding fluorescent mesoporous silica nanoparticles into biocompatible nanogels for tumor cell imaging and thermo/pH-sensitive in vitro drug release. Colloids and Surfaces B: Biointerfaces,* 116, 518-525. http://_doi.org/10.1016/j.colsurfb.2014.01.044. These particles are used as shield for enzymes or proteins, as delivery vehicles for drugs because of their porous nature and greater loading efficiency; see Liu, W. T., Yang, Y., Shen, P. H., Gao, X. J., He, S. Q., Liu, H., & Zhu, C. S. (2015). *Facile and simple preparation of pH-sensitive chitosan-mesoporous silica nanoparticles for future breast cancer treatment. Express Polymer Letters,* 9(12), 1068-1075. http://_doi.org/10.3144/expresspolymlett.2015.96; Jiao, J., Li, X., Zhang, S., Liu, J., Di, D., Zhang, Y. Wang, S. (2016). *Redox and pH dual-responsive PEG and chitosan-conjugated hollow mesoporous silica for controlled drug release. Materials Science and Engineering C,* 67, 26-33. http://_doi.org/10.1016/j.msec.2016.04.091. There are a number of synthetic techniques available in the literature for the production of the silica nanoparticles; see Bao, Y., Shi, C., Wang, T., Li, X., & Ma, J. (2016). *Recent progress in hollow silica: Template synthesis, morphologies and applications. Microporous and Mesoporous Materials,* 227, 121-136. http://_doi.org/10.1016/j.micromeso.2016.02.040. By properly selecting the synthetic route, it is possible to control the physical and chemical characteristics of silica nanoparticles. According to the end use or application of silica particles, one can design a nanostructure having desired particle size, shape, porosity, crystallinity etc.; see Chen, A., Yu, Y., Lv, H., Zhang, Y., Xing, T., & Yu, Y. (2014). *Synthesis of hollow mesoporous silica spheres and carambola-like silica materials with a novel resin sphere as template. Materials Letters,* 135, 43-46. http://_doi.org/10.1016/j.matlet.2014.07.155; Dong, Y., Wang, E., Yu, L., Wang, R., Zhu, Y., Fu, Y., & Ni, Q. Q. (2017). *Self-templated route to synthesis bowl-like and deflated balloon-like hollow silica spheres. Materials Letters,* 206, 150-153. http://_doi.org/10.1016/j.matlet.2017.07.016.

Generally adopted methods for the synthesis of hollow silica spheres include the sol-gel process and template assisted synthesis. The shape of nanoparticles can be modified by adding various dopants as precursors, changing pH or temperature during synthesis, or starting with a uniquely shaped template. There have been many approaches in creating templated or hollow silica nanoparticles using techniques such as condensation of trialkoxysilanes onto polymer based templates, metal organic frameworks (MOFs), and other nanomaterials or even island type growth using smaller nanoparticles onto a template followed by dissolution or calcination. These techniques can produce particles which are hollow and capable of carrying very large payloads or contain cores made of desirable materials such as gold, silver, or various polymers; see Liberman, A., Mendez, N., Trogler, W. C., & Kummel, A. C. (2014). *Synthesis and surface functionalization of silica nanoparticles for nanomedicine. Surface Science Reports,* 69(2-3), 132-158. https://_doi.org/10.1016/j.surfrep.2014.07.001.

Hah et al. (2003) and Wang, Liu, and Yan (2007) synthesized monodispersed phenyl functionalized hollow silica spheres by a two-step method without using templates, they obtained hollow silica spheres that are soluble in organic solvents; see Hah, H. J., Kim, J. S., Jeon, B. J., Koo, S. M., & Lee, Y. E. (2003). *Simple preparation of monodisperse hollow silica particles without using templates. Chemical Communications,* 1712-1713. http://_doi.org/10.1039/B301521A; Wang, Q., Liu, Y., & Yan, H. (2007). *Mechanism of a self-templating synthesis of monodispersed hollow silica nanospheres with tunable size and shell thickness. Chemical Communications,* (23) 2339-2341. https://_doi.org/10.1039/b701572k. For the preparation of hollow silica particles, a similar two-step method based on the sol-gel process was followed in this study; see Aslan, A., Soydan, A. M., & Bozkurt, A. (2015). *Synthesis and characterization of novel multifunctional polymer grafted hollow silica spheres. Journal of Materials Research,* 30(16), 2408-2416. http://_doi.org/10.1557/jmr.2015.222. In the first step, the hydrolysis of phenyl trimethoxysilane (PTMS) was performed under acidic conditions. In the second step, the condensation of the silane progressed under basic conditions, resulting in production of monodispersed hollow silica.

Although many wound-healing studies have involved chitosan and modified chitosan (such as chitosan blends, composites or derivatives), there are many significant challenges which need to be explored in process of wound healing; see Ahmed, S., & Ikram, S. (2016). *Chitosan based scaffolds and their applications in wound healing. Achievements in the Life Sciences,* 10(1), 27-37. http://_doi.org/10.1016/j.als.2016.04.001. For example, a wound dressing should be non-allergenic and non-toxic, maintain a moist environment, allow gas exchange, and protect a wound against growth of microbial organisms and absorb wound exudates; see Croisier, F., & Jérôme, C. (2013). *Chitosan-based biomaterials for tissue engineering. European Polymer Journal,* 49(4), 780-792. https://_doi.org/10.1016/j.eurpolymj.2012.12.009. Moreover, effective dressings should have characteristics engineered for a particular type of wound at a reasonable low cost and with minimum inconvenience to patients. Thus, while many attempts and results have been reported, successful engineering of new chitosan-based products requires a more extensive characterization of chitosan-based as well as its use in combination with various nanomaterials.

In view of the limitations of prior materials and with the objectives described above in mind, the inventors sought to more extensively study and characterize the effects of particular modes of producing chitosan-functionalized hollow silica spheres and their physical and biological properties. As disclosed herein, chitosan-functionalized hollow silica spheres were prepared by epoxidizing the HSS and then chemically binding chitosan onto the epoxidized HSS via ring opening reaction. The potential of the chitosan-modified HSS material or CHI-HSS was then evaluated for its capacity to close wounds using an in vitro scratch assay.

BRIEF SUMMARY OF THE INVENTION

Embodiments of the invention include a method for treating a wound, lesion, lacuna, or burn comprising contacting it with a chitosan-functionalized silica sphere or CHI-HSS; chitosan-functionalized silica spheres and pharmaceutical compositions containing them, and methods for making chitosan-functionalized silica spheres by epoxidating HSS with epichlorohydrin and reacting the epoxy units with amino groups on chitosan.

BRIEF DESCRIPTION OF THE SEVERAL VIEWS OF THE DRAWING(S)

FIG. 1A. Schematic representation of production of epoxidated hollow silica spheres.

Figure 1C:
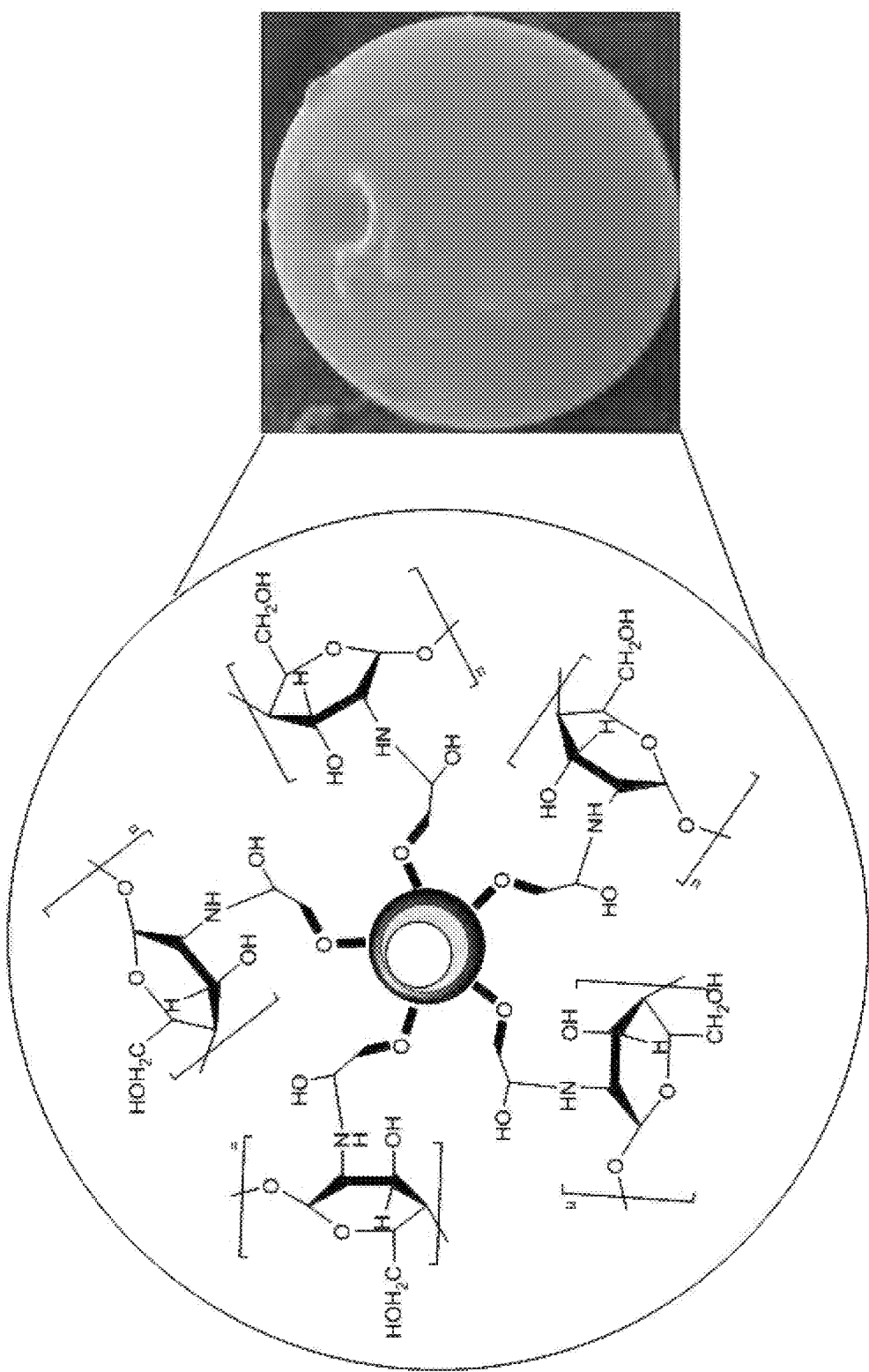
Figure 1D:
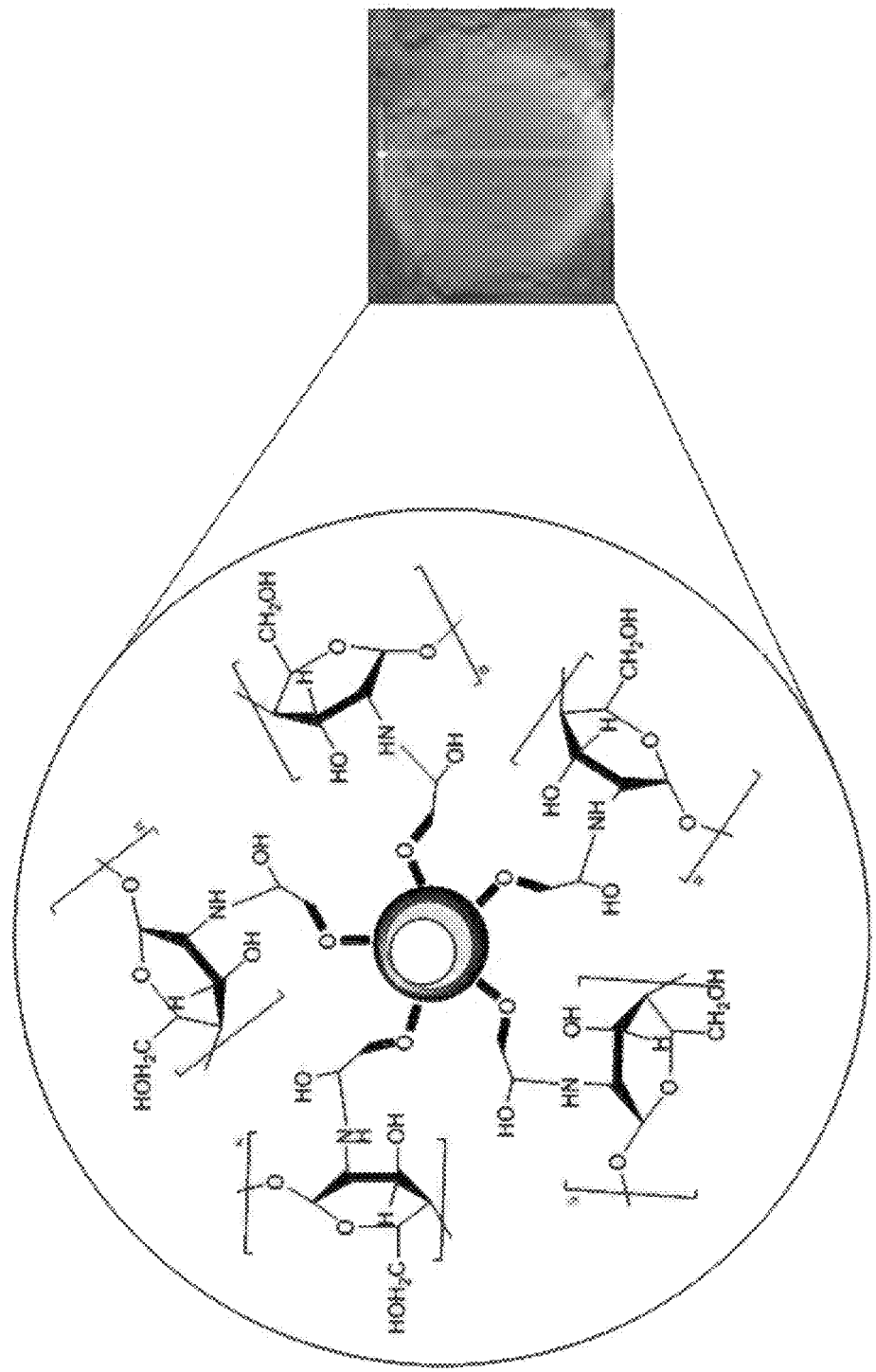
Figure 1E:
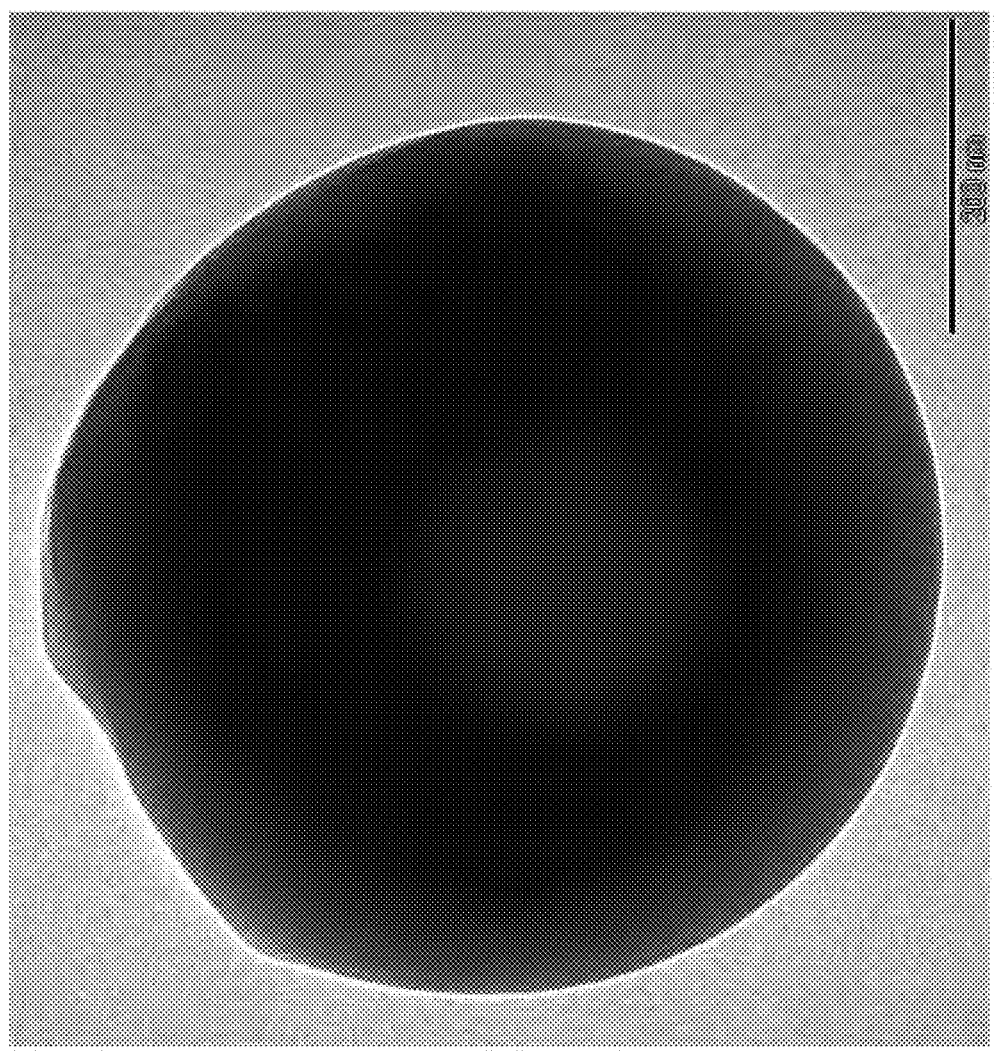

FIGS. 1B, 1C, 1D, and 1E. Schematic representation of functionalization of HSS with chitosan (FIG. 1B) and graphic representation of chitosan-functionalized hollow silica spheres (FIGS. 1C, 1D, and 1E).

Figure 2:
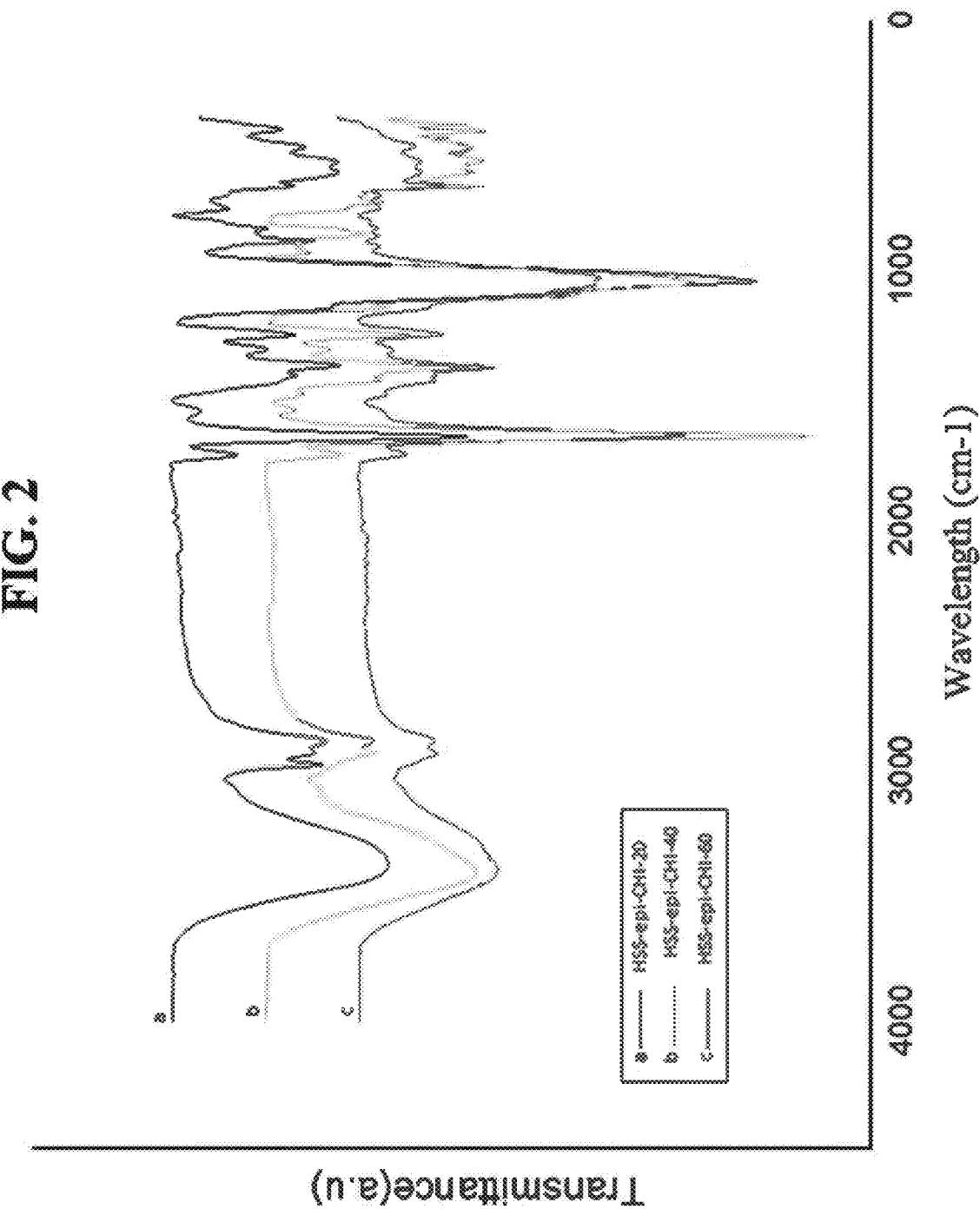

FIG. 2. FT-IR Spectra of (a) HSS-epi-CHI 20, (b) HSS-epi-CHI 40 and (c) HSS-epi-CHI 60.

Figure 3:
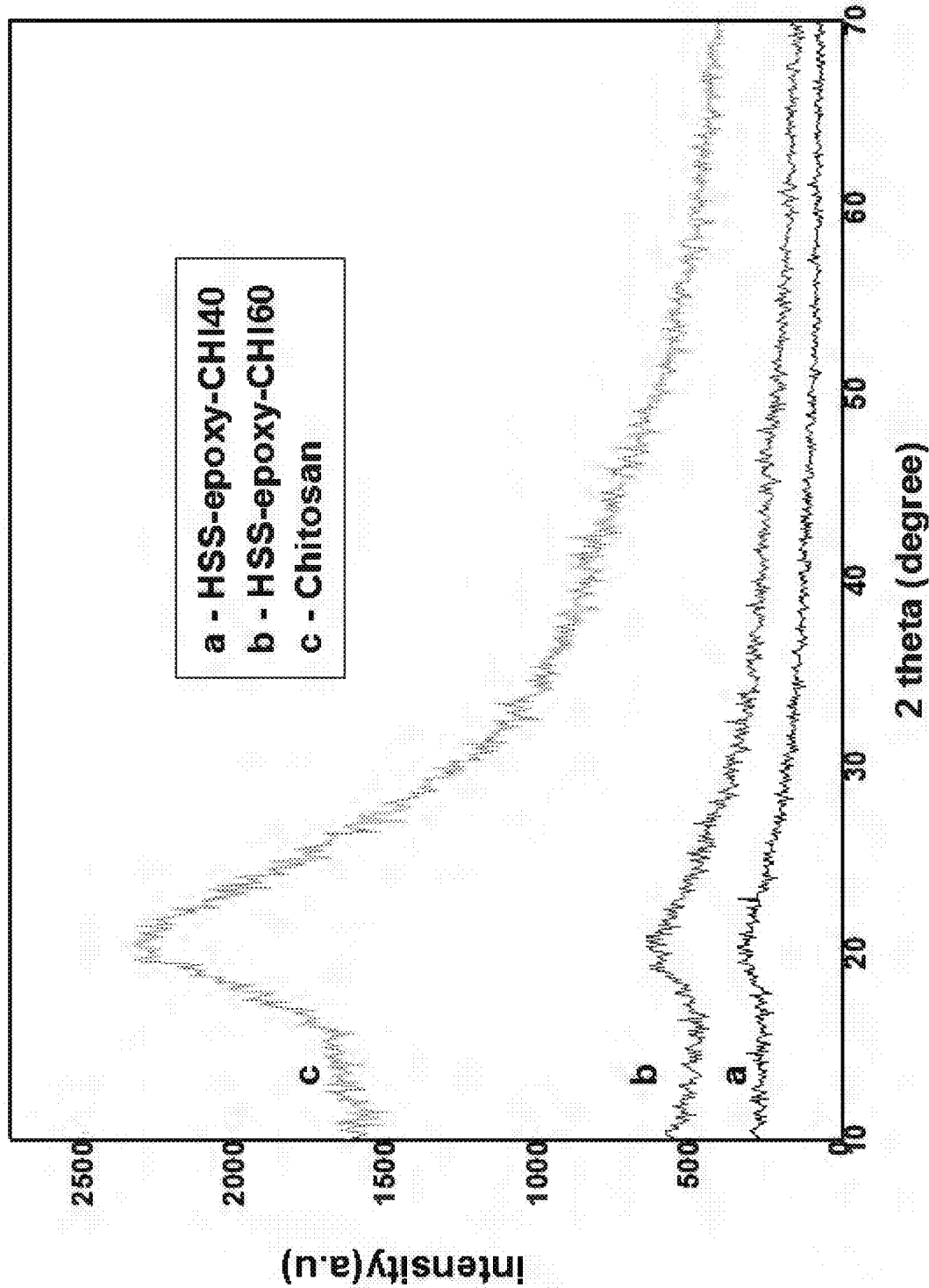

FIG. 3. XRD spectra of (a) HSS-epoxy-CHI 40, (b) HSS-epoxy-CHI 60 and (c) pure chitosan.

Figure 4A:
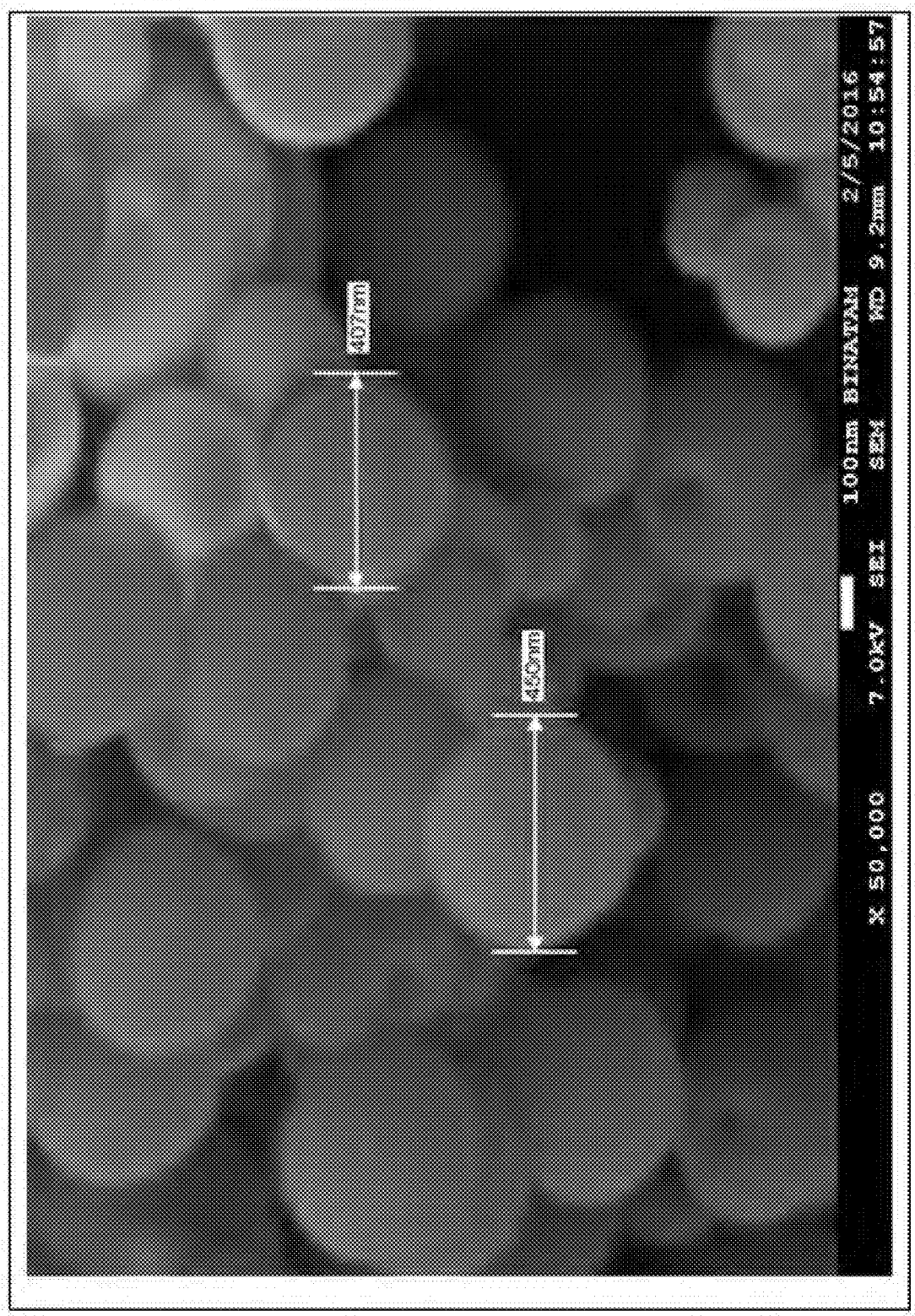

FIG. 4A. Surface morphology of chitosan-modified hollow silica sphere was analyzed by SEM.

Figure 4B:
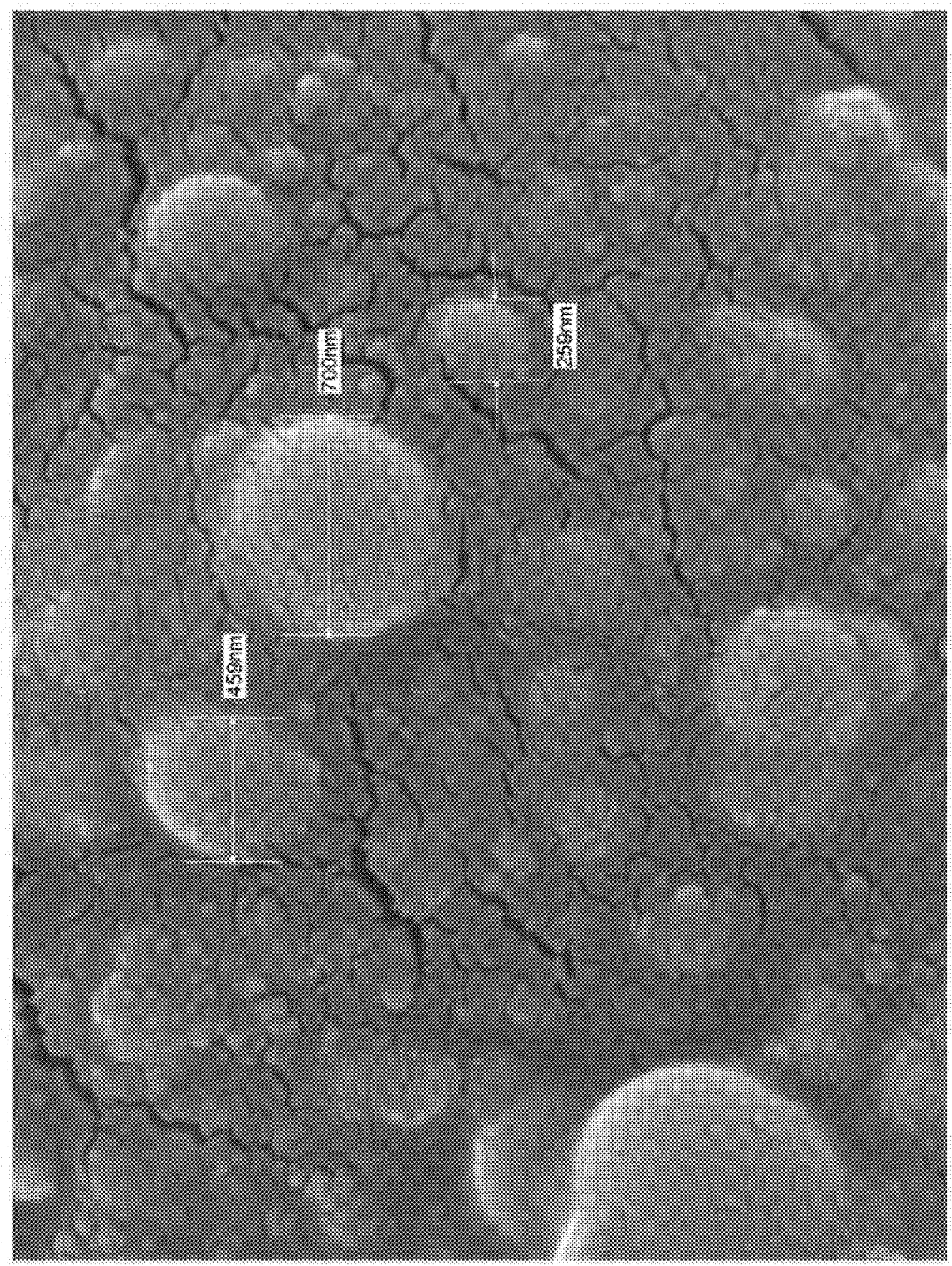

FIG. 4B. Surface morphology of chitosan-modified hollow silica sphere was analyzed by SEM.

Figure 5:
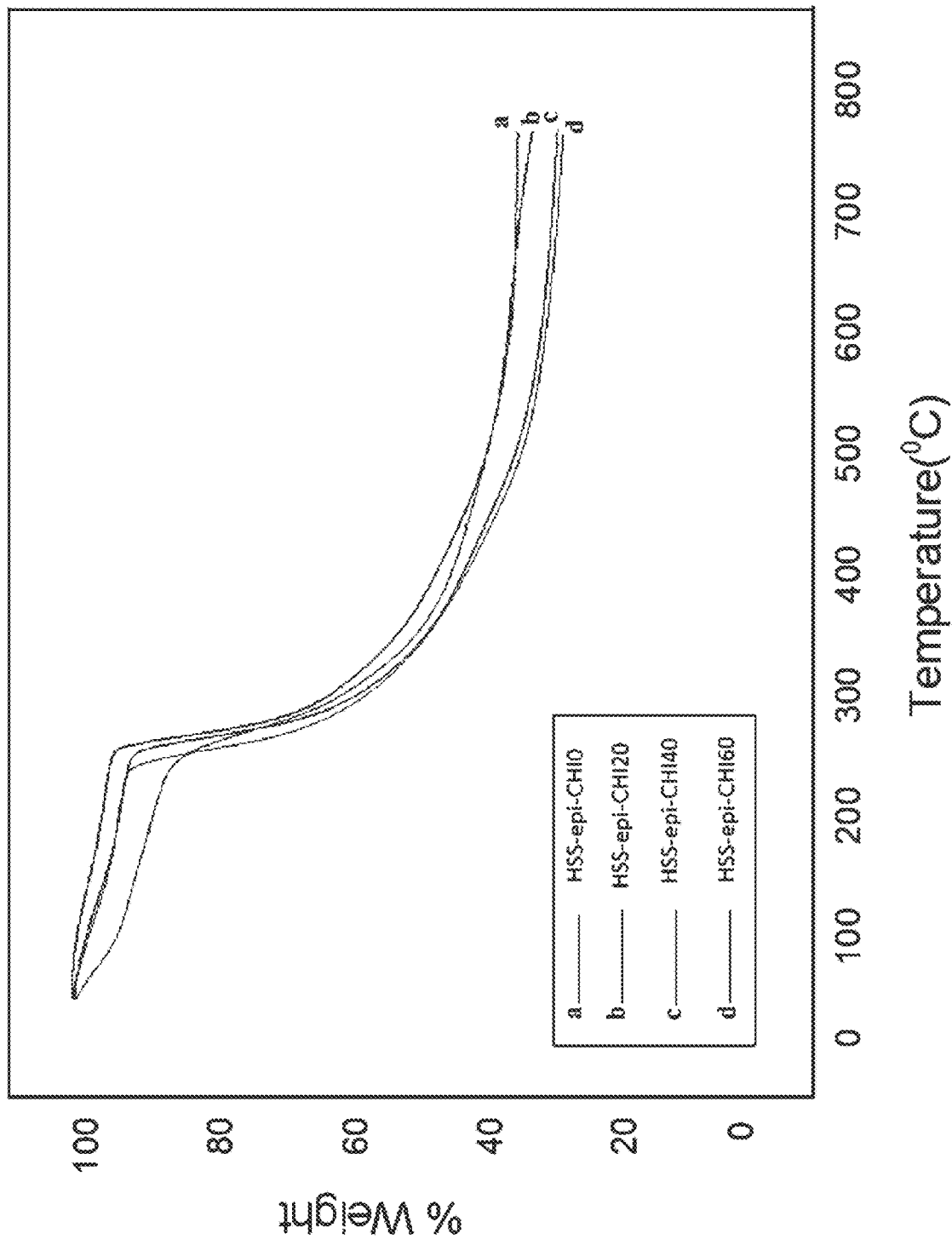

FIG. 5. Thermograms of HSCHI TGA plots of weight loss versus temperature.

FIG. 6A. Cytotoxicity assay showing % viability after exposure to various HSS formulations. Bar values show mean±SEM, n=9 from a total of three repeated experiments, *: $p<0.001$, **: $p=0.0018$, and #: $p<0.0286$ compared to untreated controls; HSS: hollow silica spheres, EPI: epichlorohydrin, Chi: chitosan.

Figure 6B:
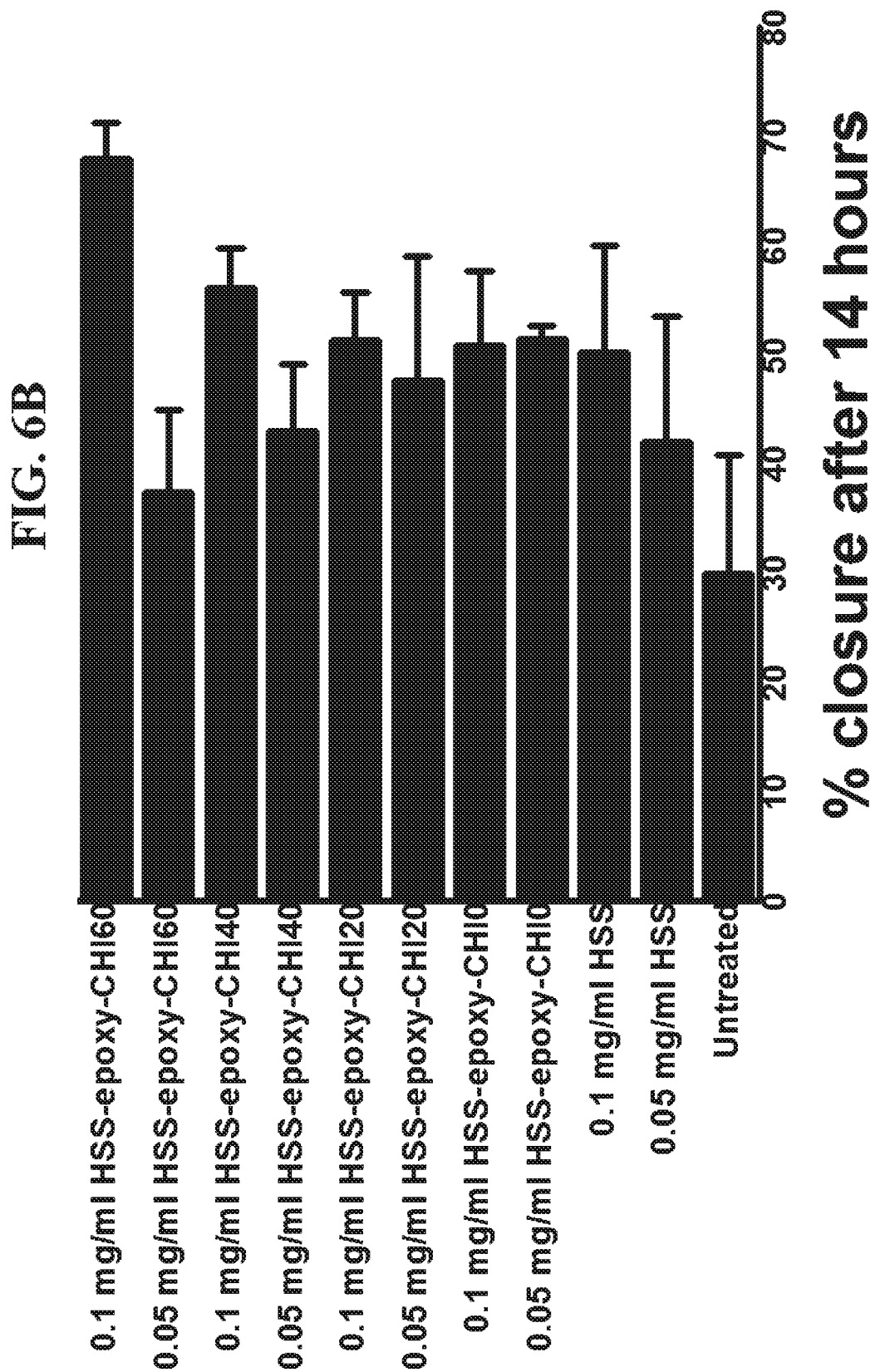

FIG. 6B. The wound healing potential of novel HSS-based formulations in in vitro wound healing assay 14 hours after the scratch & exposure to different formulation (mean±SEM, n=4 from a total of four repeated experiments, *: $p<0.05$ and **: $p<0.01$ compared to untreated controls).

Figure 6C:
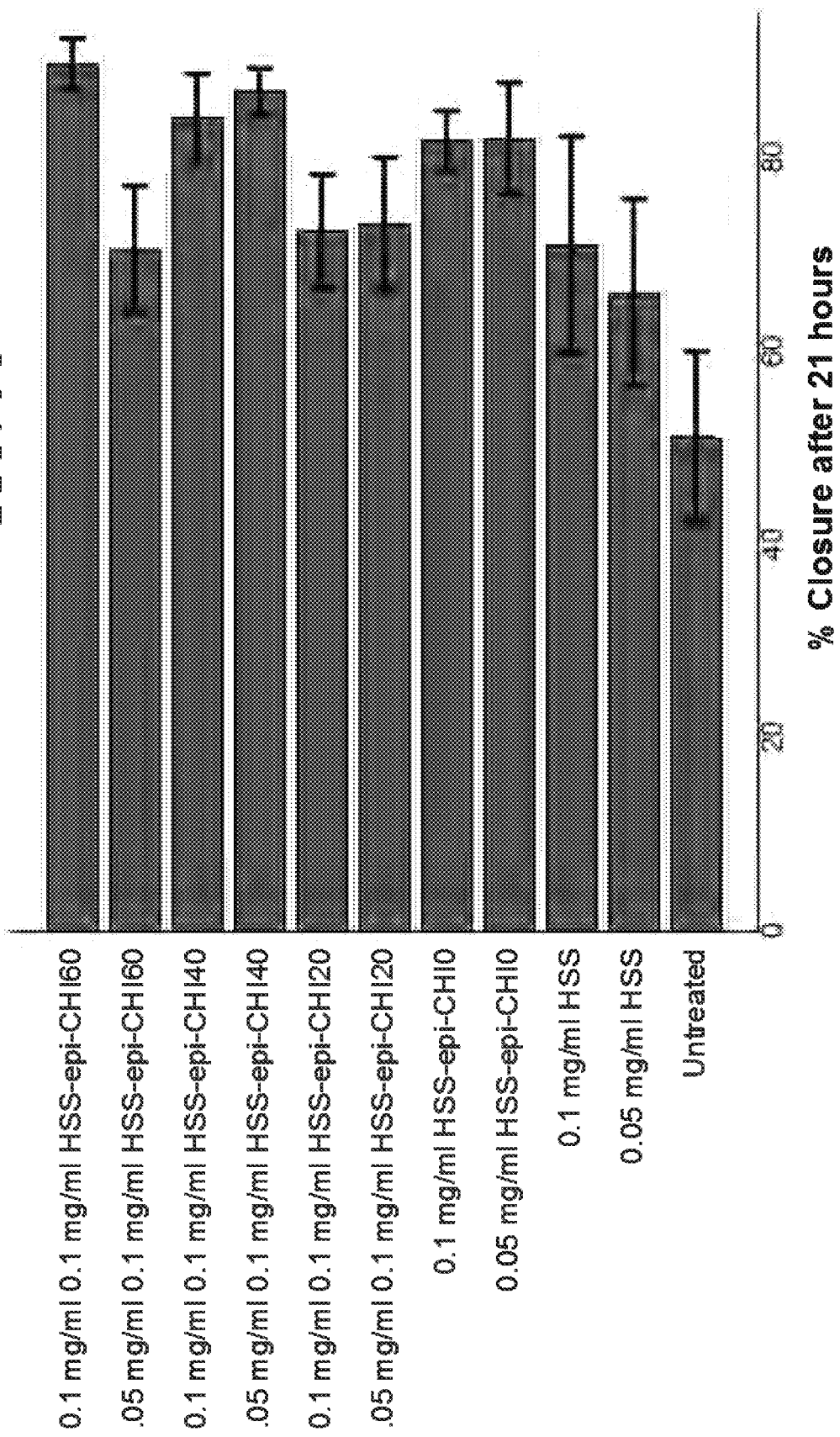

FIG. 6C. The wound healing potential of novel HSS-based formulations in in vitro wound healing assay 21 hours after the scratch & exposure to different formulation (mean±SEM, n=4 from a total of four repeated experiments, *: $p<0.05$ and **: $p<0.01$ compared to untreated controls).

FIGS. 7A-7R. The photomicrographs of in vitro scratch test at 0, 14 and 21 hours after the scratch & exposure to different Chitosan-HSS based formulations (mean±SEM, n=4 from a total of four repeated experiments, *: $p<0.05$ and **: $p<0.01$ compared to untreated controls) (100×magnification).

FIG. 8. A depiction of chitosan chemical structure.

DETAILED DESCRIPTION OF THE INVENTION

In view of the drawbacks and limitations with prior methods of wound treatment, the inventors studied and investigate new types of methods and compositions to facilitate or accelerate wound healing. They found that chitosan-functionalized HSS provided a superior wound healing effect to methods using HSS alone or chitosan alone.

The chitosan functionalized HSS can achieve a good wound healing effect. Chitosan, is a useful biopolymer for wound healing process, which was employed to carry out in vitro. In vitro scratch assay studies, it is demonstrated that chitosan modified hollow silica sphere better performance than other systems.

In this method, hollow silica spheres are chemically linked the chitosan biopolymers and they are used in wound healing applications. This new product is proposed for faster healing of the wound. It is observed that hollow silica (spherical silica) is suitable for wound healing because of its non-toxic structure.

The invention includes a wound healing bionanocomposite material production method which enables faster healing of chitosan biopolymers used in wound healing.

Definitions/Components

Nanoparticles such as HSS are characterized by a diameter, or average diameter, ranging from 1 to 1,000 nm, from 100 to 900 nm, or from 250 to 750 nm or any intermediate value of subrange within these ranges, for example, from 1, 2, 5, 10, 20, 50, 100, 200, 300, 400, 500, 750, <1,000 or 1,000 nm in diameter or average diameter.

The shell thickness of the HSS is tunable; see Zhang, et al., Hollow Silica Spheres: Synthesis and Mechanical Properties; *Langmuir* 2009, 25, 2711-2717 (incorporated by reference). Some representative shell thicknesses are between 10 and 100 nm. Advantageously, the HSS according to the invention may have an overall diameter (shell+void) ranging from 250 to 750 nm. For example, void size may be selected to fall within the range 100, 125, 150, 175, 200, 225, 250, 275, 300, 325 or 350 nm, preferably from 150-300 nm (these ranges includes all intermediate values and subranges). Shell thickness may be selected to fall within the range 75, 100, 125, 150, 175, 200, 225 or 250, preferably from 100-200 nm (these ranges include all intermediate values and subranges.

Chitosan describes chitosan derived from natural sources such as from chitin as well as chemically modified forms of chitosan that can be bound to HSS, especially via linkage between an amino group on chitosan and an epoxy group on a HSS, and which exhibit at least one biological characteristic of unmodified chitosan such as an antimicrobial, anti-inflammatory, or wound healing property. Some chitosan derivatives or modified chitosans are described by and incorporated by reference to Mourya, et al., Reactive and Functional Polymers 68(6):1013-1051 (2008), Alves, et al., Int. J. Biol. Macromol. 43(5):401-414 (2008), Li, et al., Int. J. Biol. Macromol. 75: 378-387 (2015), and Sashiwa, et al., Biomacromol. 3:1126-1128 (2002). HSS. Hollow silica spheres. HSS may be produced by known methods such as those described in the Background section and by Aslan, et al., J. Materials Res. Volume 30, Issue 16, 28 Aug. 2015, pp. 2408-2416 Synthesis and characterization of novel multifunctional polymer grafted hollow silica spheres. While not being limited to any particular protocol, HSS particles may be produced by a two-step method based on the sol-gel process as described by Aslan, et al. HSS grafted with PGMA by free radical polymerization of (glycidyl methacrylate) (GMA) and HSPGMA (PGMA grafted HSS) modified with 5-aminotetrazole (ATet), 3-amino-1,2,4-triazole (ATri), and 1H-1,2,4-triazole (Tri) to obtain 1,2,4-triazole functional PGMA grafted HSS (HSPGMA-Tri), 5-aminotetrazole functional PGMA grafted HSS (HSPGMA-Tet) and 5-Amino-Triazole functional PGMA grafted HSS (HSPGMA-ATri) molecules via ring opening of the epoxide ring.

CHI-HSS. Chitosan-functionalized hollow silica spheres.

In vivo. Many embodiments of the invention are performed in vivo or on a living body, such as on a wound or burn in the skin of a human or non-human animal.

Ex vivo. The invention may be used in conjunction with ex vivo conditioning or repair and retransplanation to accelerate healing of reperfusion injuries or surgical wounds, for example, during ex vivo procedures involving lung, kidney, dermal, or vascular explants. Injured or wounded tissue is contacted with chitosan-functionalized HSS before, during or after a retransplantation procedure.

Lacunas include gaps, punctures, cuts, scratches, scrapes, abrasions, separations, missing portions, or other unfilled spaces, intervals or voids in or between cells or tissues.

Human subjects include an embryo or fetus in utero, a premature infant, an neonate, a child less than 1, 2, 3, 4, 5, 6, 7, 8, 9, 10, 11, 12, 13, 14, 15, 16, 17, or 18 years old. An adult of at least 18, 19, 20, 21, 25, 30, 35, 40, 45, 50, 55, 60, 65, 70, 75, 80, 85, 90, 95 or 100 years old. A person having a first, second or third degree burn or a thermal, freeze, chemical or radiological burn. A person having an explosion or blast injury. A person having a crush injury or other internal or non-open wound. A person having an abrasion, puncture, penetration, gunshot wound, explosion or blast wound, incision, laceration, avulsion or other wound. A person having a surgical wound or sutured wound. A person having an autoimmune, neoplastic, or infectious lesion. A person having a non-healing or chronic wound or lesion, such as diabetic or venous ulcers. A subject who has undergone or is undergoing a tissue transplant or a recipient of a bioengineered material or tissue. Subjects at risk of developing scars, including hypertrophic scars or keloids, or desiring to minimize scar formation by application of a chitosan-functionalized HSS to a wound at risk of scarring.

Non-human subjects include invertebrates or vertebrates having wounds as described herein. Nonhuman subjects include fish, amphibians, reptiles, birds such as falcons, hawks, parrots, canaries, cockatiels, doves, ostriches, emus, chickens, turkeys, geese, Guinea fowl, quail, partridges, pheasants, and ducks, mammals such as domesticated animals including primates, horses, cattle, cows, oxen, buffalo, bison, water buffalo, goats, sheep, llamas, elephants, zebras, giraffes, rhinoceroses, camels, dromedaries, rodents, pigs, hippopotami, whales, porpoises, dolphins, or koalas, kangaroos or other marsupials.

Protease inhibitors include inhibitors of zinc endopeptidases, such as matrix metalloproteases or MMPs (including MMP2 and MMP-9), elastases, cathepsin G, and urokinase-type plasminogen activator, and serine proteases. Serine proteases and their inhibitors such as serpins (e.g., alpha-1-antichymotrypsin, C1 inhibitor, alpha-1-antitrypsin, anti-thrombin II, antithrombin III, alpha-2-antiplasmin, and pancreatic trypsin inhibitor) are described at http://www.biology-pages.info/S/Serine_Proteases.html (last accessed Dec. 28, 2017) which is incorporated by reference. Other protease inhibitors or regulators include tissue inhibitors of metalloproteinases (TIMPs). MMP inhibitors include doxycycline, an antibiotic that is also a competitive inhibitor of MMPs. One or more protease inhibitors or regulators may be administered along with or in conjunction with a chitosan-functionalized HSS of the invention during one or more phases or stages of wound healing, for example, the hemostasis phase, the inflammatory phase, the proliferation phase, and the remodeling phase.

Other Active Agents. One or more drugs, biologics or other agents may be administered along with or in conjunction with the chitosan-functionalized HSS of the invention during one or more phases of wound healing. These other active agents include an antibiotic, an anesthetic, and a steroid as well as other conventional compositions applied to burns or wounds.

Would healing assays have been used to study cell migration as well as interactions between cells. A scratch assay is disclosed herein to evaluate wound healing. Scratch assays also include those described by Rodriguez, Luis G.; Wu, Xiaoyang; Guan, Jun-Lin (2005). *Methods in Molecular Biology*, Volume 294. Humana Press. pp. 23-29. PMID 15576902; and Jonkman, James E. N.; Cathcart, Judith A.; Xu, Feng; Bartolini, Miria E.; Amon, Jennifer E.; Stevens, Katarzyna M.; Colarusso, Pina (Sep. 3, 2014). "*An introduction to the wound healing assay using live-cell microscopy*". Cell Adhesion & Migration. 8 (5): 440-451. doi: 10.4161/cam.36224. ISSN 1933-6918 (last accessed Dec. 27, 2017). All scratch assays described above of are incorporated by reference and may be used to evaluate the presence or degree of wound healing provided by the chitosan-functionalized HSS of the invention.

Therapeutic Compositions of the Invention. The compositions disclosed herein include those which contain a chitosan-functionalized HSS and which may be formulated to allow for administration to a subject by any chosen route, including but not limited to topical, oral or nasal (including by inhalation), vaginal, rectal or parenteral (including topical, subcutaneous, intramuscular and intravenous) administration. Those skilled in the art will appreciate that the route of administration to a subject will typically take into account the purpose for which the composition is being administered, for example, where a pharmaceutical composition of the invention is being administered to treat a condition, disease or disorder, the route of administration will typically be chosen taking into account the nature of the condition, disease or disorder. For example, compositions for the treatment of wounds in the skin, nail, scalp, mucosal membranes, superficial wounds, or deep skin wounds may be formulated for topical administration.

A pharmaceutical composition useful according to the invention may be formulated with an appropriate pharmaceutically acceptable carrier, such as with an excipient, diluent, auxiliary, and combinations thereof, that has been selected with regard to the intended route of administration and standard pharmaceutical practice.

The preparation of pharmaceutically acceptable carriers and formulations suitable for containing a chitosan-functionalized HSS is described in *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

pH. A composition containing a chitosan-functionalized HSS may have an acidic or basic pH, preferably from 3 to 9, more preferably from 5.5 to 8.5. It may match or coordinate to the pH of the skin (e.g., from pH 4 to 7.0, preferably about pH 5) or other organic material or tissue to which it is applied. The pH may vary upward or downward by about 0.1, 0.2, 0.5, 1.0, 1.5, or 2.0 pH units from a neutral pH or from the pH of skin or other tissue to which it is applied.

Compositions useful herein include any composition that is able to carry or incorporate a chitosan-functionalized HSS of the invention. Compositions may be prepared as solutions, serums, lotions, creams, pastes, ointment/salves, gels, aerosols, foams and other conventional formulations using known carriers for such applications. Such formulations may be administered directly, for example, applied directly on to a site of infection, burn, abrasion, acne, a wound, or sprayed onto a burn, wound or surgical site or may be applied indirectly, such as by impregnation into a bandage or dressing or sprayed onto surgical equipment, dressings and the like.

Ingredients used for one formulation described herein may be used in other formulations also described herein provided that the amounts used are compatible with the physical properties and form of the particular formulation. For example, an emulsifier or antioxidant used in a lotion may also be used in a cream, gel or foam provided it does not substantially affect the fundamental nature of the cream, gel or foam or substantially negate the wound, burn or lesion healing properties of chitosan-functionalized HSSs.

Some ingredients will modify the physical or functional characteristics of a composition. Stabilizers, preservatives, humectants, regreasing agents, solvents or auxiliaries can be included to improve efficacy and dermal penetration. Dermal penetration-enhancing compounds provided have low toxicity to the skin and can promote percutaneous and oral mucosal absorption. In one embodiment, dermal penetration-enhancing compounds include propylene glycol, polyethylene glycol, dimethylsulphoxide, decylmethylsulphoxide, azoles, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants. Viscosity enhancers or thickeners can be included.

Spreading oils or emollients can be included. One benefit for including such oils is for better distribution on surfaces, in particular on the skin. Spreading oils are understood as those oily liquids which are distributed particularly easily on the skin and are known as such in cosmetics. Suitable spreading agents include silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelators, such as disodium EDTA or sodium citrate, tackifying agents, fragrances and other compounds.

Solutions. A solution containing chitosan-functionalized HSSs, according to the invention may contain an active chitosan-functionalized HSS component and a liquid carrier suitable for dissolving, suspending, or emulsifying the chitosan-functionalized HSS. Concentrations of a chitosan-functionalized HSS in a solution or other therapeutic composition described herein may range from >0, 0.001, 0.002, 0.005, 0.01, 0.02, 0.05, 0.1, 0.2, 0.5, 1.0, 2.0, 5.0, 10.0, 20.0, 50.0 and <100 wt % of chitosan-functionalized HSS.

In some embodiments a mixture of chitosan-functionalized HSS having different wt % of chitosan in the CHI-HSS particles or a different average particle diameters may be administered. When mixtures of different chitosan-functionalized HSS are formulated, the relative amount by weight of each type of chitosan-functionalized HSS may range from 1, 2, 5, 10, 20, 25, 30, 35, 40, 45, 50, 55, 60, 65, 70, 75, 80, 85, 90, 95, <100 of the total chitosan-functionalized HSS in the composition, for example, a mixture may contain 30% by weight of CHI-HSS-20 (20 wt % chitosan based on beginning mixing ratio), 30% by weight CHI-HSS-40 (40 wt % chitosan) and 40% by weight of CHI-HSS-80 (80 wt % chitosan); or a composition may contain 50% by weight of CHI-HSSI-60 (60 wt % chitosan) and 50% by weight CHI-HSS-80 (80 wt % chitosan). The selection of mixtures of different kinds of CHI-HSS particles provides a way to tune wound healing. Advantageously a chitosan-functionalized HSS will contain based on a beginning mixiong ratio from 55, 56, 57, 58, 59, 60, 61, 62, 63, 64 or 65 wt % chitosan.

For therapeutic use a weight percentage of a solution or other composition containing CHI-HSS may correspond to the minimal dosage required to accelerate or otherwise facilitate wound healing compared to an untreated control. A solution or other therapeutic composition may be formulated to contain a concentration of 0.1, 0.2, 0.5, 1.0, 2.0, 5.0 or 10.0 or more times the minimal dosage required to induce repair of a wound, burn or lesion, preferably, the concentration in a therapeutic composition will be 1.0 or more of the minimal concentration, but is some applications a lower concentration may be used, for example, in a mixed composition containing other active ingredients or for a composition that is repeatedly applied.

Serums. A serum refers to a light, quickly absorbed composition that exposes and permits rapid uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher concentration of an active ingredient, such as chitosan-functionalized HSS, than a cream or lotion.

Lotions provided herein include liquids or semi-liquid formulations that are generally lower in viscosity than a cream or gel. The lotions can be an oil-in-water or water-in-oil formulation stabilized by a surface-active agent and are usually suitable for application to skin. They may be in a form of an emulsion and include methylcellulose, sodium carboxymethyl-cellulose, and similar compounds or contain other ingredients such as those described below for creams and other pharmaceutical compositions provided the combined amounts of the ingredients form a lotion. In one embodiment, the lotions contain suspending agents to produce better dispersions and compounds useful for localizing and holding an active agent such as a chitosan-functionalized HSS.

Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone. In another embodiment, the water phase ingredient includes, but is not limited to, glycerol and ethyl paraben. In another embodiment, the emulsifying agent includes, but is not limited to, fatty alcohol polyoxyethylene ether (Peregal A-20), polyoxylstearate (SG-6), or combinations thereof.

Ointments/salves provided herein include semi-solid preparations that have petroleum jelly or their derivatives as a base. Petroleum jelly is a semi-solid mixture of hydrocarbons. As described in *Remington: The Science and Practice* of Pharmacy, 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles or emulsified and suspended particles containing a chitosan-functionalized HSS. Black Ointment, or ichthyol Salve, also called Drawing Salve may be modified to contain a chitosan-functionalized HSS. Drawing salve has been traditionally used to treat minor skin problems such as sebaceous cysts, boils, ingrown toenails and splinters. The main ingredients are often ichthammol, phenyl alcohol, or arnica montana, and may contain herbs such as echinacea or calendula.

Pastes included herein contain, in addition to an ointment or cream base, high amounts of pulverulent constituents, such as zinc oxide, talc, starch or titanium dioxide. In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles or emulsified and suspended particles containing a chitosan-functionalized HSS.

Gels provided herein include semi-solid suspensions that contain chitosan-functionalized HSS. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In another embodiment, the organic macromolecules having a stabilizing action include long-chain linear high molecular weight polysaccharides with a molecular weight of more than one million. In another embodiment, a uniform gel can be prepared by adding dispersing agents such as alcohol or glycerin. In another embodiment, the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Hydrogels containing cross-linked insoluble starch or carboxymethylcellulose polymers and water and at least one component of the invention (e.g., a chitosan-functionalized HSS), which may contain one or more ingredients according to the invention, may be applied to skin, a burn or a wound.

Hydrocolloid dressings containing polymers such as gelatin, pectin and cellulose and at least one ingredient according to the invention which form a waterproof adhesive dressing may be used to treat a skin disorder, burn or wound. Exudates produced by the wound are absorbed into the dressing and form a gel. Hydrocolloid dressings are capable of absorbing low to moderate levels of exudate and can be used to promote autolytic debridement of dry, sloughy, or necrotic wounds.

Alginate dressings containing at least one component according to the invention may also be used for skin disorders, burns or wounds. These tend to be highly absorbent and are available in two forms; calcium alginate and calcium sodium alginate. The use of alginate dressings as hemostatic agents was reported both in vitro and in clinical studies. The selection of an alginate dressing is usually to manage wound exudate, as it is claimed that they can absorb 15-20 times their own weight in wound fluid. The alginate forms a gel when it comes into contact with the wound surface. It can be used in granulating, epithelializing, and cavity wounds. Other compositions suitable for incorporating a chitosan-functionalized HSS, especially for wounds such as diabetic ulcers, are described by Kavitha, et al., World J Diabetes. 2014 Aug. 15; 5(4): 546-556 which is incorporated by reference.

Aerosols as provided herein include products packaged under pressure and contain ingredients that are released upon activation of an appropriate valve system. Aerosols include all self-contained pressurized products, such as fine mists of spray or foam, that are emitted from a pressurized container containing a propellant, foams or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions in a container having a spray means, such as an atomizer or nebulizer. An aerosol may contain solid or encapsulated particles, emulsified and suspended particles, or liquid or atomized droplets containing a chitosan-functionalized HSS. Care should be taken in administering aerosols as in some forms or dosages chitosan may induce inflammation or allergic responses when administered into the respiratory system, eye or other sensitive tissues.

Foams. In some embodiments, a chitosan-functionalized HSS is delivered to the body while in a foam state, such as stable foam, for example, that is produced with or without a propellant. For example, the CHI-HSS may be contained in a shaving foam and used to facilitate healing of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foam may be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," issued to Lapidus on Nov. 16, 2004, herein incorporated by reference. The Lapidus patent involves the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, a surfactant is present in an amount from about 2% to about 35% by weight, or from about 5% to about 15% by weight (or any inter mediate value or subrange).

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%. The ranges above include all intermediate values and subranges.

A foam may be produced using the F2 Finger Pump Foamer™ manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference.

Encapsulation. The chitosan-functionalized HSSs described herein can be encapsulated in a carrier such as in liposomes, micelles, or microspheres. Suitable carriers are described in U.S. Pat. No. 7,205,003, hereby incorporated by reference.

Sustained-release formulations may be prepared. Suitable examples of sustained-release preparations include semipermeable matrices of solid hydrophobic polymers containing the desired antifungal agents. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate). Compositions useful herein may be adapted for immediate, delayed, modified, sustained, pulsed or controlled release of a compound of the invention. For example, a wound dressing or composition applied to the skin may be formulated to release the active compounds over a period of 1-24 hours or 1-14 days or any intermediate point in time, e.g., where skin or a treatment site is substantially immobilized such as for patients immobilized in a bed or covered by a cast, bandage, etc.

Suppositories. In addition to the active chitosan-functionalized HSSs, a suppository may contain the customary water-soluble or water-insoluble excipients, for example polyethylene glycols, fats, for example cocoa fat and higher esters (e.g., $C_{14}$-alcohol with $C_{16}$-fatty acid) or mixtures of these substances. A suppository is a drug delivery system that is inserted into the rectum (rectal suppository), vagina (vaginal suppository) or urethra (urethral suppository), where it dissolves or melts and is absorbed into the local tissues or blood stream. They are used to deliver both systemically and locally acting medications. For example, a suppository may be used to deliver a chitosan-functionalized HSS to a tear or other wound in the mucosal lining of the vagina, urethra or rectum.

Tablets, Capsules, Pills. In some embodiments, the chitosan-functionalized HSSs will be formulated as a tablet, capsule or pill. These may contain the customary excipients, such as fillers and extenders, for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcohol, glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be formulated to release the active chitosan-functionalized HSS component at a particular location within the GI tract, e.g, to transit the stomach and release the active component in the small or large intestine.

Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent.

Powders may be formulated to contain dry, encapsulated, or other anhydrous or solid forms of chitosan-functionalized HSS and one or more customary excipients, for example, lactose, talcum, silicic acid, aluminum hydroxide, calcium silicate, and polyimide powder, or mixtures of these substances. Such powders may be formulated for topical application or for internal administration. For example, a powder containing a chitosan-functionalized HSS may be applied to the surfaces of an unsutured, sutured or glued wound or burn to speed healing or joinder of wounded or burned tissues.

Personal Care Products may be formulated to contain a chitosan-functionalized HSS. Such products may be used on a regular or intermittent basis to treat microabrasions, microtears, or otherwise facilitate or promote growth of skin or other tissue. Damage caused by cosmetic surgery, such as microabrasion, chemical or enzyme peels, or by laser treatment may be treated by contacting the treated or damaged tissue with a composition containing chitosan-functionalized HSS.

Such compositions may be in the form of a dermal nourishment, dermal repair, or dermal regenerative composition, or a burn or wound-treating composition as well in the form of a composition formulated to prevent or treat irritated, burned, sunburned, infected, lesioned, acne, or dry, cracked, or rough skin.

The chitosan-functionalized HSS may be incorporated into conventional personal care products such as shampoos, body washes, lotions, lubricants, antiperspirants, or deodorants. Compositions to which a chitosan-functionalized HSS may be added include those products well known in the art and commercially available such as those described by Broad, U.S. Pat. No. 4,252,789, which is incorporated by reference.

Cosmetic compositions that can be formulated to contain chitosan-functionalized HSSs include nail care compositions to promote healing of hang nails or other minor injuries around a nail or makeup products that contain a color deposited onto a keratinous substrate such as skin, lips, and lashes. Other makeup products that may include chitosan-functionalized HSSs include primers, lipstick, lip gloss, lip plumper, lip liners, lip balms, eyeliners, eyeshadows, masara, concealers, rouges, foundations, face powders, highlighters, contour powders or creams, bronzers, eyebrow definers, and setting sprays for makeup.

A cosmetic composition can be in many different forms, including liquid or cream emulsions; powders that are pressed, cast, or loose; dispersions, foams, and anhydrous creams or sticks; or solids such as pencils and the aforementioned powders and sticks; shower and bath compositions containing the liphophilic hydroxytyrosol carbonate ester compounds include but are not limited to body washes (including a moisturizing, reparative, or regenerating body wash), shower gels, skin cleansers, cleansing milks, in shower body moisturizer, and pet shampoo; hair care compositions include shampoos, hair conditioners, colorants, dyes, bleaches, straighteners, and permanent wave products; infant care compositions include infant shampoo, infant body wash, and infant bubble bath; skin care compositions include shaving compositions, cleansing compositions, emollients, moisturizing compositions including anti-aging compositions; exfoliant compositions, face masks, and skin toners, and compositions containing pharmaceutically active ingredients for reduction of skin irritations, rashes, inflammations, and excema; and sun care compositions including compositions containing UV blocking agents (UVA and/or UVB), such as sun tan compositions, sunscreen compositions having an SPF rating of 20 or more, or 30 or more, or 40 or more, or 50 or more; and lip balms and lip care for protection against wind and sun. Sun care compositions may also include sunless tanning treatments.

Buccal, dental and oral compositions. A composition according to the invention may be formulated for administration by mouth, onto a mucous membrane, or into our around a gastric ulcer or intestinal lesion, especially to locations or tissues in need of repair, for example, cuts or lesions in the mouth or GI tract, receding or damaged gum tissue. Such compositions include washes as well as liquids and foods suitable for oral consumption.

Parenteral or ex vivo. While many applications of this technology are directed to direct in vivo treatment of external burns, wounds and lesions, in cases where there are internal wounds or tissues in need of repair, or other wounds, burns and lesions which would benefit from oral or parenteral modes of administration a parenteral or oral composition containing chitosan-functionalized HSS may be administered.

Parenteral or ex vivo dosage forms include aqueous solutions, isotonic saline or glucose solutions comprising the active agent, or other well-known pharmaceutically acceptable carriers. Solubilizing agents well-known to those familiar with the art can be used as pharmaceutical excipients. Injectable dosage forms may be formulated as liquid solutions or suspensions. A composition for parenteral administration may be formulated to be locally injected to a site of an internal burn, lesion, lacuna, or wound or may be formulated for systemic administration. Solid forms suitable for dissolving in, or suspending in, pharmaceutically acceptable liquid prior to injection may also be prepared.

In vitro. In some embodiments, the invention may be formulated for use in vitro, for example, to facilitate growth, regrowth, attachment, reattachment or joinder of cells or tissues in vitro, such as for repair of damaged or scratched cellular monolayers or for joinder of different kinds of monolayers or tissues cultured in vitro. In such embodiments the chitosan-functionalized HSS may be incorporated into a culture medium or wash, or applied directly to portions of a monolayer or to cultured cells.

EMBODIMENTS

Non-limiting embodiments of the invention include:

Embodiment 1

A method for treating a wound, burn, lesion, or lacuna comprising contacting the wound, burn, lesion, or lacuna with a chitosan-functionalized hollow silica sphere ("CHI-HSS"). This embodiment also embraces any tissue or cellular structure or condition in need of healing, repair, restoration, rejuvenation, or growth, for example, joinder or repair of tissues or groups of cells via proliferation of fibroblasts or other cells that form or join cells or tissues together.

Embodiment 2

The method of embodiment 1, wherein the CHI-HSS contains 40-80 wt % chitosan and have an average diameter of 200 to 600 nm. In some embodiments the CHI-HSS will contain less than 100, 95, 90, 85, 80, 75, 70, 65, 60, 55, 50, 45, 40, 35, 30, 25, 20, 15, 10, 5, 2 or 1 wt % chitosan. The amount of chitosan in a CHI-HSS may vary by 1, 2, 5, 10, 15, 20, 25% of the specified wt % of chitosan, for example, a CHI-HSS may contain 30 wt % chitosan±0.3, 0.6, 1.5, 3, 4.5, 6, or 7.5 wt % chitosan. This range includes all intermediate values and subranges.

Embodiment 3

The method of embodiment 1 that comprises contacting the wound, burn, lesion or lacuna with a composition containing a concentration of at least 0.05 mg/ml of CHI-HSS. In some embodiments, the wound, burn, lesion, or lacuna may be treated with a higher or lower concentration of a CHI-HSS. Generally, the concentration used for treatment will meet or exceed the minimum amount required to induce, promote or otherwise facilitate wound healing compared to an untreated control or a control treated with HSS only or chitosan not bound to HSS alone. In some embodiments a concentration of 0.01, 0.02, 0.05, 0.1, 0.2, 0.5, 1.0, 2.0, 5.0, 10, 20, 50, 100, 200, 500 mg/ml of CHI-HSS or a mixture of different types of CHI-HSS will be used for treatment.

A wound, burn, lesion or lacuna may be contacted with a CHI-HSS for a time sufficient to initiate, promote or otherwise facilitate healing or joinder of cells or tissues. For example, it may be contacted one time with a composition containing CHI-HSS, may be intermittently or periodically contacted with CHI-HSS, or may be continuously contacted with CHI-HSS. In some embodiments, the period of contacting will range from 1 second, 1 minute, 1 hour, 1 day, 2 days, 1 week, 2 weeks, one month or a period sufficient to at least partially heal a wound or at least partially join or repair cellular layers or other structures or tissues. This time range includes all intermediate values and subranges.

Embodiment 4

The method of embodiment 1, further comprising contacting said the CHI-HSS with the wound, burn, lesion, or lacuna at a pH of at least 4.0 but less than 7.0. In some embodiments, contacting may occur at a pH of at least 4, 4.5, 5, 5.5, 6, 6.5 or <7. In other embodiments, were a neutral or alkaline environment is desired (for example, in an early phase of tissue repair or wound healing where the activity of proteases or other factors active at a neutral or alkaline pH are desired), contact may occur at a pH of at least pH 7, 7.5., 8.0, 8.5 or 9.0.

Embodiment 5

The method of embodiment 1, further comprising contacting said the CHI-HSS with the wound, burn, lesion, or lacuna in the presence of at least one protease inhibitor. In some embodiments, contacting of CHI-HSS will take place in the presence of a protease inhibitor, for example, during later stages of wound healing where proteolysis of healing tissues is not desired. Protease inhibitors of proteases active during wound repair or healing are known in the art and are described elsewhere herein. A suitable concentration of a protease inhibitor may be selected to inhibit 10, 20, 50 or 100% of the proteolytic activity of one or more proteases active during wound or burn repair or healing. This concentration range includes all intermediate values and subranges.

Embodiment 6

The method of embodiment 1, wherein said contacting occurs during a cellular proliferation phase or maturation or remodelling healing phase.

Embodiment 7

The method of embodiment 1 comprising contacting the CHI-HSS with an abrasion, puncture, penetration, gunshot or ballistic wound, explosion or blast wound, incision, laceration, avulsion or other wound.

Embodiment 8

The method of embodiment 1 comprising contacting the CHI-HSS with a surgical wound. Surgical wounds include, but are not limited to those described at http://_www.med.umich.edu/surgery/mast/r_surgwoundclass.html (last accessed Dec. 29, 2017), the text available at this link is hereby incorporated by reference. Some examples of surgical wounds include clean, clean-contaminated, contaminated, and dirty wounds. In some embodiments, the chitosan-HSS will be coadministered along with a conventional therapy for a surgical wound, such as an antibiotic, cleaning and disinfection regimen.

Embodiment 9

The method of embodiment 1 comprising contacting the CHI-HSS with a chronic wound or nonhealing wound. In some embodiments, the CHI-HSS will be contacted with a hematoma, crush injury, or other closed wound.

Embodiment 10

The method of embodiment 1 comprising contacting the CHI-HSS with an electrical, radiological, UV, solar, chemical, freeze, thermal, or other burn.

Embodiment 11

The method of embodiment 1 comprising contacting the CHI-HSS with a lesion caused by or associated with an allergy, autoimmune event, infection, or neoplasm.

Embodiment 12

The method of embodiment 1, wherein the burn, lesion, lacuna, or wound is on a human body.

Embodiment 13

The method of embodiment 1, wherein the burn, lesion, lacuna, or wound is on a nonhuman mammal, avian, or other animal body.

Embodiment 14

The method of embodiment 1, wherein the burn, lesion, lacuna, or wound is on tissue maintained or cultured ex vivo or in vitro.

Embodiment 15

A pharmaceutical composition comprising a chitosan-functionalized hollow silica sphere ("CHI-HSS") and a pharmaceutically acceptable carrier or excipient.

Embodiment 16

The pharmaceutical composition of embodiment 15, wherein the chitosan-functionalized hollow silica spheres range in average diameter from 250 to 750 nm.

Embodiment 17

The pharmaceutical composition of embodiment 15, wherein the chitosan-functionalized hollow silica spheres are porous and permeable to water.

Embodiment 18

A method for making a chitosan-functionalized hollow silica sphere comprising producing a hollow silica sphere comprising hydroxyl groups, converting the hydroxyl groups into epoxy groups, and functionalizing the epoxy groups by chemically bonding chitosan to them.

Embodiment 19

The method of embodiment 18, wherein the hollow silica spheres are functionalized with epichlorohydrin and the resulting epoxy groups on the epichlorohydrin-functionalized hollow silica spheres are reacted with amino groups on chitosan, thereby providing a chitosan-functionalized hollow silica sphere.

Embodiment 20

A chitosan-functionalized hollow silica sphere produced by the method of embodiment 18.

As shown by the following, non-limiting examples, hollow silica spheres (HSS) (nanoparticles) were synthesized by sol-gel process and functionalized with chitosan. The chitosan-functionalized hollow silica spheres were characterized by FT-IR spectroscopic analysis, X-ray diffraction studies, thermogravimetric analysis and morphology studies by scanning electron microscopy. A cytotoxicity assay showed that the chitosan-functionalized nanoparticles were nontoxic and an in vitro scratch assay demonstrated the superior wound healing capacity of the chitosan-functionalized HSS compared to controls.

EXAMPLES

Chitosan Functionalization

Phenyl trimethoxysilane (PTMS) (97%), epichlorohydrin (99%), low molecular weight chitosan (mol. wt 50,000-190,000 Da, Deacetylated 75-85%) and DMF were purchased from Sigma Aldrich. Other chemicals used in the synthesis such as $HNO_3$, $NH_4OH$ were of analytical purity. HSS nanoparticles were prepared as reported in the inventors' previous work; see Aslan, A., Soydan, A. M., & Bozkurt, A. (2015). *Synthesis and characterization of novel multifunctional polymer grafted hollow silica spheres. Journal of Materials Research,* 30(16), 2408-2416. http://_doi.org/10.1557/jmr.2015.222. Briefly, a sol-gel method was adopted for developing HSS. Phenyl trimethoxysilane (PTMS) was hydrolyzed in acidic medium ($HNO_3$) and condensation of the HSS was performed in basic medium ($NH_4OH$) (FIG. 1A). The precipitated nanoparticles were collected by a membrane filter and washed with water and ethanol and were dried under vacuum.

For carrying out the epoxidation, the dried HSS was dissolved in DMF and epichlorohydrin was added drop wise to the solution at RT. During the reaction, HCl gas was released from the solution. Then temperature was increased to 70° C. for 1 hr. The modified hollow silica spheres were recovered (FIG. 1B).

The next step included binding of chitosan on to the functionalized hollow silica sphere surface via ring opening reaction, see FIG. 1B. Stoichiometric amounts of chitosan were added to the solution of epoxidized HSS at 70° C. and stirred for 3 hr. HSS-epoxy-CHI was precipitated. The precipitate was washed with water/methanol solution several times. Then, the product was filtered and dried at 80° C. under vacuum. Different HSS-epoxy-CHI samples were prepared by varying the weight percentage of chitosan, e.g., to 20 wt %, 40 wt %, 60 wt % and 80 wt %. The formulation of the samples used in the present study is given in the Table below.

| Sample Code | Chitosan Composition |
| --- | --- |
| HS-epoxy-CHI-0 | 0 |
| HS-epoxy-CHI-20 | 20 wt % |
| HS-epoxy-CHI-40 | 40 wt % |
| HS-epoxy-CHI-60 | 60 wt % |
| HS-epoxy-CHI-80 | 80 wt % |

Prior to characterization, the samples were dried under vacuum and stored in a glove box.

Characterization of Functionalized Nanospheres IR Spectra

The IR spectra (4000-400 $cm^{-1}$, resolution 4 $cm^{-1}$) were recorded with a Bruker Alpha-P in Attenuated Total Reflectance (ATR) system. Thermal stabilities of the samples were examined by thermogravimetry analysis (TGA) with a Perkin Elmer STA 6000. The samples (~10 mg) were heated from room temperature to 700° C. under $N_2$ atmosphere at a heating rate of 10° C. $min^{-1}$. X-ray data were obtained from a fully automated 9.0 kW anode rotating generator Rigaku Smart Lab X-Ray Diffractometer with 2 theta range 0 to 70°. The surface morphologies of the samples were observed by scanning electron microscopy (SEM, Philips XL30S-FEG). All of the samples were sputter-coated with gold for 150 seconds prior to SEM analysis.

Infrared spectra of chitosan functionalized HSS samples i.e., HSS-epoxy-CHI-20, HSS-epoxy-CHI-40, HSS-epoxy-CHI-60 are shown in FIG. 2. The absorption peaks at 1080 $cm^{-1}$ and 802 $cm^{-1}$ are typical of Si—O—Si bonds. The absorption band at 1000-1100 was increased in intensity increase owing to the absorption from the Si—O—C bonds. The band centered at 954 $cm^{-1}$ is associated with the stretching mode of non-bridging oxide bands as Si—OH and Si—O; see Aslan, A., & Bozkurt, A. (2010). *Bioinspired blend membranes based on adenine and guanine functional poly(glycidyl methacrylate). Langmuir,* 26(16), 13655-13661, https://_doi.org/10.1021/1a102096y. Addition of epoxy units on HSS was confirmed by methylene peaks centered at 2900 $cm^{-1}$ and some broader peaks located near 1590 $cm^{-1}$. The absorption which is expected at 900 $cm^{-1}$ was assigned to stretching vibration of the epoxy group and was masked by Si—O—Si peaks; see Nanjundan, S., Unnithan, C. S., Selvamalar, C. S. J., & Penlidus, A. (2005), *Homopolymer of 4-benzoylphenyl methacrylate and its copolymers with glycidyl methacrylate: synthesis, characterization, monomer reactivity ratios and application as* adhesives. *Reactive and Functional Polymers*, 62(1), 11-24. https://_doi.org/10.1016/j.reactfunctpolym.2004.08.006; Asian, A., & Bozkurt, A. (2010). *Bioinspired blend membranes based on adenine and guanine functional poly(glycidyl methacrylate)*. Langmuir, 26(16), 13655-13661. https://_doi.org/10.1021/la102096y.

The signals at 3328 and 3174 $cm^{-1}$ were assigned to —NH and —OH modes from the ring and the amino groups. A peak at 1654 $cm^{-1}$ corresponds to amide I group and a combined vibration of C=O stretching and the —N—H deformation mode. Other signals were assigned as follows: 1590 $cm^{-1}$ to —N—H deformation, at 1423 $cm^{-1}$ amine group band, —C—N axial deformation at 1380 $cm^{-1}$-$CH_3$ deformation, at 1152 $cm^{-1}$; β(1-4) glycosidic bond in the polysaccharide unit, at 1080 $cm^{-1}$ amine —C—N stretching vibration), and in the range of 1080-1020 $cm^{-1}$-CH—OH stretching in cyclic compounds; see Liu, Y. L., Su, Y. H., & Lai, J. Y. (2004). *In situ crosslinking of chitosan and formation of chitosan-silica hybrid membranes with using γ-glycidoxypropyltrimethoxysilane as a crosslinking agent*. Polymer, 45(20), 6831-6837; https://_doi.org/10.1016/j.polymer.2004.08.006. The absorption band at 1550 $cm^{-1}$ belongs to —N—H bending of the primary amine salt.

Thermal Stabilities

Thermogravimetric analysis of chitosan functionalized HSS materials were performed under $N_2$ atmosphere at a scan rate of 10° C. $min^{-1}$ TGA plots of chitosan functional used HSS samples are shown in FIG. 5. TGA graph of chitosan usually follows a two-step degradation profile. A small weight loss can be observed within the temperature range 30 to 180° C. due to the evaporation of absorbed water and small molecules, major weight loss occurs between 250 to 600° C. due to the decomposition of chitosan polymer chains and also due to the degradation of phenyl groups of HSS; see Zhao, Y., Yan, N., & Feng, M. W. (2013). The degradation characteristics of phenol-formaldehyde resins derived from beetle infested pine barks. *Thermochimica Acta*, 555, 46-52. https://_doi.org/10.1016/j.tca.2012.12.002. TGA plots of chitosan functionalized HSS samples showed similar pattern, only slight variation in thermal stability was observed. There was small variation in the initial weight loss of the analyzed samples, which represents the variation in the moisture content in the samples. The residue content of the samples was proportionate with the chitosan content in it. Sample prepared with low chitosan content showed higher residue content and samples with high chitosan content showed less residue content because of the full degradation of the chitosan molecules. FIG. 5 depicts the TGA curves of chitosan functionalized HSS samples.

Cytotoxicity Assay

To investigate the cytotoxic potential of novel hollow silica-based nanoparticles in vitro, each of the freshly synthesized formulations was incubated with HepG2 cells. HepG2 cells are conventionally used in cytotoxicity assays; see Bao, et al., Biomed Environ Sci, 2012; 25(5): 495-501; and Senthilraja, et al., Journal of Applied Pharmaceutical Science Vol. 5 (03), pp. 080-084, March, 2015.

Human liver carcinoma cells (HepG2) were seeded in a 24-well plate at $1\times10^5$ cells/well and cultured overnight at 37° C. and 5% $CO_2$. The cells were cultured in medium composed of DMEM supplemented with 2 mM L-glutamine, 100 U/ml penicillin, 100 µg/ml streptomycin, 4.5 g/l glucose, and 10% FBS.

Concentrations of 0.01, 0.1 and 1 mg/ml (i.e., 10, 100, or 1000 µg/ml) of various formulations of nanoparticles were added to the cells and incubated for 24 hours.

Following a 24-hour incubation, an MTT-based assay was used to assess the cellular viability.

All wells were washed with PBS and incubated with 0.3 mg/ml of MTT (3-(4,5-dimethylthiazol-2-yl)-2,5-diphenyltetrazolium bromide) at 37° C. for 3 hours.

The resulting formazan crystals were solubilized in 450 µL of DMSO and absorbance was measured at 570 nm by a UV-vis spectrophotometer.

FIG. 6A statistically compares a control (Unt., untreated) value with samples treated with the various kinds of chitosan-derivatized. HSS. As shown there, the in vitro cytotoxicity analysis confirmed the safety of HSS and chitosan-functionalized HSS. Unmodified HSS were not toxic at concentrations up to 100 µg/ml but exhibited significant cytotoxicity of about 20% at 1 mg/ml. HSS modified with epichlorohydrin and chitosan were also nontoxic at lower concentrations. HSS modified with epichlorohydrin and chitosan showed improved cell viability at 1 mg/ml, compared to that of unmodified HSS. HSS formulations that contained 20 wt %, 40 wt %, and 60 wt % of chitosan showed no cytotoxicity even at the highest dose of treatment.

Scanning Electron Microscopic Analysis

The XRD patterns of the chitosan (c) and CHI-HSS with a chitosan content of 40% (a) and 60% (b) are shown in FIG. 3. Pure chitosan (c) showed a strong peak 2θ=20.5 as reported in literature; see Flores, C., Lopez, M., Tabary, N., Neut, C., Chai, F., Betbeder, D, Blanchemain, N. (2017). *Preparation and characterization of novel chitosan and β-cyclodextrin polymer sponges for wound dressing applications*. Carbohydrate Polymers, 173, 535-546. https://_doi.org/10.1016/j.carbpol.2017.06.026. The hollow silica spheres were amorphous in nature and no crystalline peaks were observed, except one broad band around 22°; see Chen, J. J., Li, H. J., Zhou, X. H., Li, E. Z., Wang, Y., Guo, Y. L., & Feng, Z. S. (2017). *Efficient synthesis of hollow silica microspheres useful for porous silica ceramics*. Ceramics International, 43(16), 13907-13912. https://_doi.org/10.1016/j.ceramint.2017.07.118. For chitosan functionalized HSS samples, the intensity of this small peak increased with the increase in the percentage of chitosan in the samples, attributing to the presence of chitosan in the samples.

The surface morphology of synthesized HSS and chitosan functionalized HSS were analyzed by SEM. The SEM image of HSS in FIG. 4A confirms the hollow/porous nature of HSS. The synthesized HSS showed an average diameter of 400 nm. FIG. 4B represents the SEM image of chitosan functionalized HSS (40 wt % chitosan). It can be seen that HSS particles were homogeneously dispersed in chitosan and no phase separation was observed between chitosan and HSS, after modification of hollow silica spheres with chitosan via ring opening reaction of epoxy. It is expected that the pores on the HSS are permeable for water vapor and wound exudates. It has been reported that the permeability of d exudate can prevent bullae formation; see Hinrichs, W. L., Lommen, E. J., Wildevuur, C. R., & Feijen, J. (1992). *Fabrication and characterization of an asymmetric polyurethane membrane for use as a wound dressing. Journal of*

Applied Biomaterials: An Official Journal of the Society for Biomaterials, 3(4), 287-303. https://_doi.org/10.1002/jab.770030408.

Thermal Analysis

The thermal stability of the CHI-HSS functional material was measured. The CHI-HSS functional samples were placed under an inert atmosphere and analyzed at a scan rate of 10° C. min$^{-1}$. Pure chitosan is thermally stable up to 180° C. The large weight loss in the temperature range from 180° C. to 600° C. in the synthetic sample is probably attributable to the decomposition of chitosan polymer. FIG. 5 shows the thermograms of CHI-HSS TGA plots of weight loss versus temperature provide an estimate of the quantity of chitosan units from the HSS. After functionalization from the particle, TGA shows a total weight loss of 70%, which corresponds to chitosan functionalization ratio, is approximately 70%. Reaction of chitosan functionalization leads to a total weight loss of approximately 70% which is consistent with essentially complete functionalization between chitosan units and the hollow silica sphere (HSS) nanoparticles.

In Vitro Wound Healing (Scratch) Assay

NIH 3T3 fibroblasts cells were seeded in 12-well plates at 1×10$^5$ cells/well and grown until confluence in complete DMEM supplemented with 10% FBS, 2 mM L-glutamine, 100 U/ml penicillin, 100 µg/ml streptomycin, and 4.5 g/l glucose in a humidified chamber at 37° C. and 5% $CO_2$. In order to simulate a wound, a straight scratch was made in each well with a P200 pipette tip. The cell debris was removed and the cells were treated with various formulations of nanoparticles for 24 hr. The closure of the scratch was observed under the microscope at certain time intervals i.e., 0, 14 and 21 hours after the scratch and the treatment with nanoparticles. Digital images of cells were captured by a phase contrast microscope (Leica). The closure of the scratch was calculated based on the width difference initially and after 14 to 21 hours of treatment, using the Image J software (National Institutes of Health, Bethesda, Md., USA) and expressed as percentage of scratch closure.

Skin is the largest body organ, which protects the human body by acting as a passive barrier and preventing harmful pathogens from entering. However, skin can be wounded or damaged by a physical, a chemical or a thermal event. Wounds and burns are serious problems in health care. Wound healing is a complex process that involves the regeneration of the damaged tissues and replacement of lost tissues. The wound healing process has been characterized to go through four phases: hemostasis, inflammation, proliferation, and remodeling; see Sinno, & Prakash, 2013. In wound healing, chitin and chitosan often function to activate to fibroblasts, produce cytokines, induce giant cell migration and stimulate type IV collagen synthesis.

To investigate the wound healing potential of chitosan functionalized HSS nanoparticles (CHI-HSS), each of the newly synthesized formulations in DMSO was tested by in vitro wound healing assay. The wound was simulated by introducing a straight scratch in a confluent culture of NIH 3T3 fibroblasts. FIGS. 6B and 6C describe the wound healing potential of novel HSS-based formulations in in vitro wound healing assay at 14 hours and at 21 hours, respectively, after the scratch & exposure to different formulation (mean±SEM, n=4 from a total of four repeated experiments, *: p<0.05 and **: p<0.01 compared to untreated controls.

At 14 and 21 hours later, the percent closure was observed and calculated as described in the materials and methods section. 14 hours after introducing a scratch and treating with different formulations, only 100 µg/ml of HSS formulation containing 60 wt % chitosan had significantly higher percent closure of about 70%, that is, healing, compared to the untreated controls with average percent closure of about 30%, see FIG. 6B. All of the remaining formulations showed slightly higher but not statistically significant increase in percent closure of the initial scratch. At 21 hours after introducing a scratch and exposure to different formulations, the average percent closure of untreated control is increased to about 50%, see FIG. 6C. Whereas, every HSS formulation showed average percent closure higher than the controls with most of the formulations having a statistically higher increase in percent closure, see FIG. 6C. This was quite expected due to biological activity of chitosan and the hollow nature of silica that permits exudates absorption and gas exchange. Similar to the 14 hour treatment period, the 100 µg/ml of HSS formulation containing 60 wt % chitosan had the highest percent closure of about 90%.

FIGS. 7A-7R show photo micrographs of scratch analysis at various time intervals, i.e., at 0, 14 hours and 21 hours after the scratch and exposure to different chitosan-HSS formulations (concentration –0.1 mg/ml). Compared to the untreated scratch, greater percent closure was observed for the scratch treated with HSS-chitosan formulations. It was observed that as the chitosan content in the formulation increases, percent wound closure increases. Among the different formulations studied, formulation with 60 wt % chitosan content showed greater wound closure. It can be seen that, in all cases, as the exposure time increases, more closure can be achieved. Compared to 14 hours treated samples, a greater percent closure was observed after 21 hours.

As shown by the Examples above chitosan functionalized hollow silica nanoparticles were prepared and characterized by different techniques such as FT-IR, TGA, XRD and SEM. These novel biocompatible nanoparticles were non-toxic as determined using HepG2 cells and were tested using an in vitro scratch assay using NIH 3T3 fibroblast cells for application in wound healing. Out of the analyzed nanoformulations, the sample with 60 wt % chitosan exhibited the best performance. About 70% wound closure was observed for this sample after 14 hours of exposure. A 90% wound closure was observed after 21 hours of treatment. The synergic effect of chitosan and HSS leads to better performance of these materials. From the results it can be seen that wound healing ability of the samples is proportionate to the chitosan content in the samples, concentration of nanoparticles formulation, and the exposure time. Scratches exposed to higher concentrations of chitosan nanoformulations showed round closure to a greater extent.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. The text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features, elements, or steps, these features/elements/steps are not limited by these terms unless the context indicates otherwise. These terms may be used to distinguish one feature/element/step from another feature/element/step. Thus, a first feature/element/step discussed below could be termed a second feature/element/step, and similarly, a second feature/element/step discussed below could be termed a first feature/element/step without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. For example, chitosan may be bound to a HSS directly via an bound formed between an amino group on chitosan and an epoxy group on a HSS, or may be bound to a HSS via one or more intermediate chemical groups or linkers. In contrast, when a feature or element is referred to as being "directly on" or "directly bound to" another feature or element, there are no intervening features or elements present. Thus, it will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a wound, burn, lesion, or lacuna comprising contacting the wound, burn, lesion, or lacuna with chitosan-functionalized hollow silica spheres ("CHI-HSS").

2. The method of claim 1, wherein the CHI-HSS contain 60±20 wt % chitosan and have an average diameter of 200 to 600 nm.

3. The method of claim 1 that comprises contacting the wound, burn, lesion or lacuna with a composition containing a concentration of at least 0.05 mg/ml of CHI-HSS.

4. The method of claim 1, further comprising contacting said CHI-HSS with the wound, burn, lesion, or lacuna at a pH of at least 4.0 but less than 7.0.

5. The method of claim 1, further comprising contacting said CHI-HSS with the wound, burn, lesion, or lacuna in the presence of at least one protease inhibitor.

6. The method of claim 1, wherein said contacting occurs during a cellular proliferation phase or maturation or remodelling healing phase of wound healing.

7. The method of claim 1, wherein the wound, burn, lesion or lacuna is an abrasion, puncture, penetration, gunshot wound, explosion or blast wound, incision, laceration, avulsion or other wound to the skin.

8. The method of claim 1, wherein the wound, burn, lesion or lacuna is a surgical wound.

9. The method of claim 1, wherein the wound, burn, lesion or lacuna is a chronic wound or nonhealing wound.

10. The method of claim 1, wherein the wound, burn, lesion or lacuna is an electrical, radiological, UV, solar, chemical, freeze, thermal or other burn.

11. The method of claim 1, wherein the wound, burn, lesion or lacuna is not caused by a neoplasm.

12. The method of claim 1, wherein the burn, lesion, lacuna, or wound is on a mucous membrane.

13. The method of claim 1, wherein the wound, burn, lesion, or lacuna, is on a human body.

14. The method of claim 1, wherein the wound, burn, lesion, or lacuna is on tissue maintained or cultured ex vive or in vitro.

15. The method of claim 1 wherein the chitosan-functionalized hollow silica spheres ("CHI-HSS") have an average diameter ranging from 250 to 750 nm, have a shell thickness ranging from 10 to 100 nm, and contain at least 40 wt % chitosan.

16. The method of claim 1, wherein the chitosan-functionalized hollow silica spheres range in average diameter from 300 to 500 nm, have a shell thickness ranging from 40 to 70 nm, and contain at least 60 wt % chitosan.

17. The method of claim 1, wherein the chitosan-functionalized hollow silica spheres are porous and permeable to water.

18. The method of claim 1, wherein the chitosan-functionalized hollow silica spheres are made by a process comprising producing hollow silica spheres comprising hydroxyl groups, functionalizing the hydroxyl groups with epoxy groups, and reacting the epoxy groups with chitosan in a ring-opening reaction to chemically bond chitosan to a surface of the hollow silica spheres.

19. The method of claim 18, wherein the hollow silica spheres are functionalized with epichlorohydrin and the resulting epoxy groups on the epichlorohydrin-functionalized hollow silica spheres are reacted with amino groups on chitosan, thereby providing the chitosan-functionalized hollow silica spheres.

* * * * *